(12) United States Patent
Gamache et al.

(10) Patent No.: US 9,724,132 B2
(45) Date of Patent: Aug. 8, 2017

(54) DEVICES AND METHODS FOR CERVICAL LATERAL FIXATION

(75) Inventors: Thomas J. Gamache, Fall River, MA (US); Michael Sorrenti, Middleboro, MA (US); John Riley Hawkins, Cumberland, RI (US); Michael Gorhan, Mansfield, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 13/222,776

(22) Filed: Aug. 31, 2011

(65) Prior Publication Data

US 2013/0053893 A1    Feb. 28, 2013

(51) Int. Cl.
*A61B 17/70*    (2006.01)
*A61F 2/44*    (2006.01)
(Continued)

(52) U.S. Cl.
CPC ...... *A61B 17/7062* (2013.01); *A61B 17/7007* (2013.01); *A61B 17/7011* (2013.01);
(Continued)

(58) Field of Classification Search
CPC ............ A61B 17/7007; A61B 17/7011; A61B 17/7014; A61B 17/7002; A61B 17/7025;
(Continued)

(56) References Cited

U.S. PATENT DOCUMENTS 4,170,990 A    10/1979 Baumgart et al.
4,444,181 A    4/1984 Wevers et al.
(Continued)

FOREIGN PATENT DOCUMENTS

CN    1893897 A    1/2007
CN    101056590 A    10/2007
(Continued)

OTHER PUBLICATIONS

DalCanto, et. al., Biomechanical Comparison of Transarticular Facet Screws to Lateral Mass Plates in Two-Level Instrumentations of the Cervical Spine, SPINE vol. 30, No. 8, pp. 897-902, © 2005, Lippincott Williams & Wilkins, Inc.
(Continued)

*Primary Examiner* — Jan Christopher Merene
*Assistant Examiner* — Atiya Mahmud
(74) *Attorney, Agent, or Firm* — Nutter McClennen & Fish LLP

(57) ABSTRACT

Devices and methods are provided for treatment of the cervical spine. The devices and methods allow for treatment to be delivered from a lateral or posterior-lateral location of a subject, proximate to the cervical region of the spine. One exemplary embodiment of a spinal implant includes an elongate cage member and a plate member appended to a proximal end of the cage member. The plate member can be oriented in a manner such that it is asymmetric with respect to a long axis of the cage member. In another exemplary embodiment, an implant includes a cage member having a distal end that has an asymmetrical, bulleted shape such that the distal end is biased towards a superior or cranial direction. In a third exemplary embodiment, an implant includes a spinal fixation element and at least two mounting eyelets formed thereon. Exemplary methods related to implanting spinal implants from a lateral or posterior-lateral location are also provided.

21 Claims, 25 Drawing Sheets

(51) Int. Cl.
*A61B 17/84* (2006.01)
*A61B 17/86* (2006.01)
*A61F 2/30* (2006.01)
*A61F 2/28* (2006.01)

(52) U.S. Cl.
CPC ...... *A61B 17/7014* (2013.01); *A61B 17/7059* (2013.01); *A61B 17/844* (2013.01); *A61B 17/864* (2013.01); *A61F 2/446* (2013.01); *A61F 2/4455* (2013.01); *A61F 2/4465* (2013.01); *A61F 2002/2817* (2013.01); *A61F 2002/2835* (2013.01); *A61F 2002/30062* (2013.01); *A61F 2002/3078* (2013.01); *A61F 2002/3085* (2013.01); *A61F 2002/30092* (2013.01); *A61F 2002/30578* (2013.01); *A61F 2002/30616* (2013.01); *A61F 2002/30774* (2013.01); *A61F 2002/30779* (2013.01); *A61F 2002/30785* (2013.01); *A61F 2002/30797* (2013.01); *A61F 2002/30858* (2013.01); *A61F 2002/30904* (2013.01); *A61F 2002/4475* (2013.01); *A61F 2310/00017* (2013.01); *A61F 2310/00023* (2013.01)

(58) Field of Classification Search
CPC ............ A61B 17/7041; A61B 17/7043; A61B 17/7044; A61B 17/7046
USPC .................................. 606/250–261, 264, 278
See application file for complete search history.

(56) References Cited

U.S. PATENT DOCUMENTS

| | | | |
|---|---|---|---|
| 4,448,191 A * | 5/1984 | Rodnyansky et al. | 606/250 |
| 4,485,816 A | 12/1984 | Krumme | |
| 4,573,458 A * | 3/1986 | Lower | 606/280 |
| 4,887,601 A | 12/1989 | Richards | |
| 4,913,144 A | 4/1990 | Del Medico | |
| 5,055,104 A | 10/1991 | Ray | |
| 5,123,705 A | 6/1992 | Johnson | |
| 5,129,904 A | 7/1992 | Illi | |
| 5,152,303 A | 10/1992 | Allen | |
| 5,169,400 A | 12/1992 | Muhling et al. | |
| 5,246,443 A | 9/1993 | Mai | |
| 5,314,427 A | 5/1994 | Goble et al. | |
| 5,397,364 A | 3/1995 | Kozak et al. | |
| 5,409,486 A | 4/1995 | Reese | |
| 5,443,515 A | 8/1995 | Cohen et al. | |
| 5,470,333 A * | 11/1995 | Ray | A61B 17/7055 606/261 |
| 5,489,308 A | 2/1996 | Kuslich et al. | |
| 5,501,684 A * | 3/1996 | Schlapfer et al. | 606/301 |
| 5,534,031 A | 7/1996 | Matsuzaki et al. | |
| 5,593,409 A | 1/1997 | Michelson | |
| 5,609,636 A | 3/1997 | Kohrs et al. | |
| 5,645,598 A | 7/1997 | Brosnahan, III | |
| 5,658,337 A | 8/1997 | Kohrs et al. | |
| 5,669,909 A | 9/1997 | Zdeblick et al. | |
| 5,683,463 A | 11/1997 | Godefroy et al. | |
| 5,707,372 A | 1/1998 | Errico et al. | |
| 5,709,683 A | 1/1998 | Bagby | |
| 5,743,912 A | 4/1998 | Lahille et al. | |
| 5,752,955 A | 5/1998 | Errico | |
| 5,766,253 A | 6/1998 | Brosnahan, III | |
| 5,776,196 A | 7/1998 | Matsuzaki et al. | |
| 5,779,707 A | 7/1998 | Bertholet et al. | |
| 5,782,919 A | 7/1998 | Zdeblick et al. | |
| 5,785,710 A | 7/1998 | Michelson | |
| 5,810,817 A | 9/1998 | Roussouly et al. | |
| 5,860,973 A | 1/1999 | Michelson | |
| 5,876,457 A | 3/1999 | Picha et al. | |
| 5,885,287 A | 3/1999 | Bagby | |
| 5,888,223 A | 3/1999 | Bray, Jr. | |
| 5,888,228 A | 3/1999 | Knothe et al. | |
| 5,906,616 A | 5/1999 | Pavlov et al. | |
| 5,916,267 A | 6/1999 | Tienboon | |
| 5,964,761 A | 10/1999 | Kambin | |
| 5,984,967 A | 11/1999 | Zdeblick et al. | |
| 6,010,502 A | 1/2000 | Bagby | |
| 6,045,552 A * | 4/2000 | Zucherman | A61B 17/1604 606/71 |
| 6,048,343 A | 4/2000 | Mathis et al. | |
| 6,066,175 A | 5/2000 | Henderson et al. | |
| 6,071,310 A | 6/2000 | Picha et al. | |
| 6,074,423 A | 6/2000 | Lawson | |
| 6,093,207 A | 7/2000 | Pisharodi | |
| 6,096,060 A | 8/2000 | Fitts et al. | |
| 6,099,531 A | 8/2000 | Bonutti | |
| 6,102,948 A | 8/2000 | Brosnahan, III | |
| 6,120,506 A | 9/2000 | Kohrs et al. | |
| 6,149,650 A | 11/2000 | Michelson | |
| 6,149,686 A | 11/2000 | Kuslich et al. | |
| 6,156,037 A | 12/2000 | LeHuec et al. | |
| 6,165,219 A | 12/2000 | Kohrs et al. | |
| 6,168,631 B1 | 1/2001 | Maxwell et al. | |
| 6,214,012 B1 | 4/2001 | Karpman et al. | |
| 6,231,610 B1 | 5/2001 | Geisler | |
| 6,235,059 B1 | 5/2001 | Benezech et al. | |
| 6,241,770 B1 | 6/2001 | Michelson | |
| 6,264,656 B1 | 7/2001 | Michelson | |
| 6,287,343 B1 | 9/2001 | Kuslich et al. | |
| 6,325,803 B1 | 12/2001 | Schumacher et al. | |
| 6,342,074 B1 | 1/2002 | Simpson | |
| 6,346,122 B1 | 2/2002 | Picha et al. | |
| 6,375,655 B1 | 4/2002 | Zdeblick et al. | |
| 6,391,058 B1 | 5/2002 | Kuslich et al. | |
| 6,402,757 B1 | 6/2002 | Moore, III et al. | |
| 6,428,575 B2 | 8/2002 | Koo et al. | |
| 6,432,107 B1 | 8/2002 | Ferree | |
| 6,436,141 B2 | 8/2002 | Castro et al. | |
| 6,471,724 B2 | 10/2002 | Zdeblick et al. | |
| 6,485,518 B1 | 11/2002 | Cornwall et al. | |
| 6,527,805 B2 | 3/2003 | Studer et al. | |
| 6,565,572 B2 | 5/2003 | Chappius | |
| 6,585,738 B1 * | 7/2003 | Mangione et al. | 606/258 |
| 6,589,245 B1 | 7/2003 | Weiler et al. | |
| 6,629,998 B1 | 10/2003 | Lin | |
| 6,645,206 B1 | 11/2003 | Zdeblick et al. | |
| 6,669,697 B1 * | 12/2003 | Pisharodi | 606/264 |
| 6,682,563 B2 | 1/2004 | Scharf | |
| 6,726,722 B2 | 4/2004 | Walkenhorst et al. | |
| 6,730,127 B2 | 5/2004 | Michelson | |
| 6,758,849 B1 | 7/2004 | Michelson | |
| 6,783,545 B2 | 8/2004 | Castro et al. | |
| 6,811,567 B2 | 11/2004 | Reiley | |
| 6,972,019 B2 | 12/2005 | Michelson | |
| 6,981,974 B2 | 1/2006 | Berger | |
| 7,001,385 B2 | 2/2006 | Bonutti | |
| 7,033,394 B2 | 4/2006 | Michelson | |
| 7,041,135 B2 | 5/2006 | Michelson | |
| 7,077,864 B2 | 7/2006 | Byrd, III et al. | |
| 7,090,675 B2 | 8/2006 | Songer | |
| 7,104,992 B2 * | 9/2006 | Bailey | 606/278 |
| 7,135,043 B2 | 11/2006 | Nakahara et al. | |
| 7,137,997 B2 | 11/2006 | Paul | |
| 7,163,561 B2 | 1/2007 | Michelson | |
| 7,172,627 B2 | 2/2007 | Fiere et al. | |
| 7,182,781 B1 | 2/2007 | Bianchi et al. | |
| 7,226,482 B2 | 6/2007 | Messerli et al. | |
| 7,232,463 B2 | 6/2007 | Falahee | |
| 7,232,464 B2 | 6/2007 | Mathieu et al. | |
| 7,238,203 B2 | 7/2007 | Bagga et al. | |
| 7,288,093 B2 | 10/2007 | Michelson | |
| 7,323,011 B2 | 1/2008 | Shepard et al. | |
| 7,410,789 B2 | 8/2008 | Schlosser et al. | |
| 7,442,209 B2 | 10/2008 | Michelson | |
| 7,491,237 B2 | 2/2009 | Randall et al. | |
| 7,575,580 B2 | 8/2009 | Lim et al. | |
| 7,594,931 B2 | 9/2009 | Louis et al. | |
| 7,601,173 B2 | 10/2009 | Messerli et al. | |
| 7,618,456 B2 | 11/2009 | Mathieu et al. | |
| 7,628,816 B2 | 12/2009 | Magerl et al. | |
| 7,658,754 B2 | 2/2010 | Zhang et al. | |

(56) References Cited

U.S. PATENT DOCUMENTS

| | | | |
|---|---|---|---|
| 7,749,272 B2 | 7/2010 | Robie et al. | |
| 7,850,731 B2 | 12/2010 | Brittan et al. | |
| 8,075,622 B2 | 12/2011 | Van Hoeck et al. | |
| 8,292,898 B2 | 10/2012 | Castaneda et al. | |
| 8,470,039 B2 | 6/2013 | Blain | |
| 8,591,551 B2* | 11/2013 | Miller | 606/264 |
| 9,381,048 B2 | 7/2016 | Gamache et al. | |
| 2001/0010020 A1 | 7/2001 | Michelson | |
| 2002/0040242 A1 | 4/2002 | Picha et al. | |
| 2002/0116064 A1 | 8/2002 | Middleton | |
| 2002/0138144 A1 | 9/2002 | Michelson | |
| 2002/0156529 A1 | 10/2002 | Li et al. | |
| 2002/0183846 A1 | 12/2002 | Kuslich et al. | |
| 2003/0009222 A1 | 1/2003 | Fruh et al. | |
| 2003/0100950 A1 | 5/2003 | Moret | |
| 2003/0114854 A1 | 6/2003 | Pavlov et al. | |
| 2003/0114930 A1 | 6/2003 | Lim et al. | |
| 2003/0139816 A1 | 7/2003 | Michelson | |
| 2003/0153920 A1 | 8/2003 | Ralph et al. | |
| 2003/0181981 A1 | 9/2003 | Lemaire | |
| 2004/0034430 A1 | 2/2004 | Falahee | |
| 2004/0064185 A1 | 4/2004 | Michelson | |
| 2004/0097928 A1 | 5/2004 | Zdeblick et al. | |
| 2004/0127906 A1 | 7/2004 | Culbert et al. | |
| 2004/0133277 A1 | 7/2004 | Michelson | |
| 2004/0172019 A1 | 9/2004 | Ferree | |
| 2005/0038434 A1 | 2/2005 | Mathews | |
| 2005/0038513 A1 | 2/2005 | Michelson | |
| 2005/0055099 A1 | 3/2005 | Ku | |
| 2005/0101960 A1 | 5/2005 | Fiere et al. | |
| 2005/0177245 A1 | 8/2005 | Leatherbury et al. | |
| 2005/0197700 A1 | 9/2005 | Boehm et al. | |
| 2005/0288673 A1* | 12/2005 | Catbagan | A61B 17/7007 606/281 |
| 2006/0064090 A1* | 3/2006 | Park | 606/61 |
| 2006/0064099 A1 | 3/2006 | Pavlov et al. | |
| 2006/0085071 A1 | 4/2006 | Lechmann et al. | |
| 2006/0100625 A1 | 5/2006 | Ralph et al. | |
| 2006/0106382 A1* | 5/2006 | Gournay | A61B 17/7037 606/278 |
| 2006/0129243 A1 | 6/2006 | Wong et al. | |
| 2006/0155279 A1* | 7/2006 | Ogilvie | 606/61 |
| 2006/0167548 A1 | 7/2006 | Jackson | |
| 2006/0235388 A1 | 10/2006 | Justis et al. | |
| 2006/0235426 A1 | 10/2006 | Lim et al. | |
| 2006/0235518 A1 | 10/2006 | Blain | |
| 2006/0265074 A1* | 11/2006 | Krishna et al. | 623/17.15 |
| 2007/0093833 A1 | 4/2007 | Kuiper et al. | |
| 2007/0106388 A1 | 5/2007 | Michelson | |
| 2007/0173954 A1 | 7/2007 | Lavi | |
| 2007/0233253 A1 | 10/2007 | Bray et al. | |
| 2007/0250167 A1 | 10/2007 | Bray et al. | |
| 2007/0270965 A1 | 11/2007 | Ferguson | |
| 2008/0021454 A1* | 1/2008 | Chao | A61B 17/7044 606/250 |
| 2008/0051890 A1 | 2/2008 | Waugh et al. | |
| 2008/0065217 A1 | 3/2008 | Hurlbert et al. | |
| 2008/0097447 A1* | 4/2008 | Biscup et al. | 606/71 |
| 2008/0154374 A1 | 6/2008 | Labrom | |
| 2008/0161927 A1 | 7/2008 | Savage et al. | |
| 2008/0177307 A1 | 7/2008 | Moskowitz et al. | |
| 2008/0177327 A1 | 7/2008 | Malandain et al. | |
| 2008/0249569 A1 | 10/2008 | Waugh et al. | |
| 2008/0249575 A1 | 10/2008 | Waugh et al. | |
| 2008/0249625 A1 | 10/2008 | Waugh et al. | |
| 2008/0255622 A1 | 10/2008 | Mickiewicz et al. | |
| 2008/0281425 A1 | 11/2008 | Thalgott et al. | |
| 2008/0300634 A1 | 12/2008 | Gray | |
| 2008/0306555 A1 | 12/2008 | Patterson et al. | |
| 2008/0306596 A1 | 12/2008 | Jones et al. | |
| 2008/0312742 A1 | 12/2008 | Abernathie | |
| 2009/0030519 A1 | 1/2009 | Falahee | |
| 2009/0030520 A1 | 1/2009 | Biedermann et al. | |
| 2009/0054987 A1 | 2/2009 | Chin et al. | |
| 2009/0062921 A1 | 3/2009 | Michelson | |
| 2009/0105830 A1 | 4/2009 | Jones et al. | |
| 2009/0105831 A1 | 4/2009 | Jones et al. | |
| 2009/0182430 A1 | 7/2009 | Tyber et al. | |
| 2009/0198246 A1 | 8/2009 | Lim et al. | |
| 2009/0210062 A1 | 8/2009 | Thalgott et al. | |
| 2009/0210064 A1 | 8/2009 | Lechmann et al. | |
| 2009/0240287 A1 | 9/2009 | Cunliffe et al. | |
| 2009/0306671 A1 | 12/2009 | McCormack et al. | |
| 2009/0318968 A1* | 12/2009 | Duggal et al. | 606/250 |
| 2010/0069963 A1* | 3/2010 | Eckman | 606/255 |
| 2010/0198221 A1 | 8/2010 | Hearn | |
| 2010/0204796 A1 | 8/2010 | Bae et al. | |
| 2010/0234956 A1 | 9/2010 | Attia et al. | |
| 2010/0262242 A1 | 10/2010 | Chavatte et al. | |
| 2010/0324599 A1* | 12/2010 | Montello | A61B 17/7001 606/264 |
| 2011/0015745 A1 | 1/2011 | Bucci | |
| 2011/0144693 A1* | 6/2011 | Black | 606/250 |
| 2012/0065687 A1* | 3/2012 | Ballard | A61B 17/7004 606/259 |
| 2013/0053894 A1 | 2/2013 | Gamache et al. | |
| 2015/0374510 A1 | 12/2015 | Fiechter et al. | |
| 2016/0008140 A1 | 1/2016 | Melkent et al. | |

FOREIGN PATENT DOCUMENTS

| | | |
|---|---|---|
| CN | 101180011 A | 5/2008 |
| CN | 101466321 A | 6/2009 |
| CN | 101778603 A | 7/2010 |
| EP | 369603 A1 | 5/1990 |
| EP | 0856293 A1 | 8/1998 |
| EP | 1 103 236 A2 | 5/2001 |
| EP | 1114625 A1 | 7/2001 |
| EP | 1 391 189 A1 | 2/2004 |
| EP | 1400221 A2 | 3/2004 |
| EP | 1 774 926 A2 | 4/2007 |
| EP | 1 834 608 A2 | 9/2007 |
| EP | 1 847 240 A1 | 10/2007 |
| EP | 1887990 A1 | 2/2008 |
| JP | 2002-528172 A | 9/2002 |
| WO | WO-9106261 A1 | 5/1991 |
| WO | WO-9627339 A1 | 9/1996 |
| WO | WO-9640020 A1 | 12/1996 |
| WO | 9720526 A1 | 6/1997 |
| WO | 98/04217 A1 | 2/1998 |
| WO | 9963914 A1 | 12/1999 |
| WO | 02/080819 A1 | 10/2002 |
| WO | 03/005938 A1 | 1/2003 |
| WO | 03/070128 A1 | 8/2003 |
| WO | WO-2004043278 A1 | 5/2004 |
| WO | 2004/069106 A1 | 8/2004 |
| WO | WO-2004100808 A1 | 11/2004 |
| WO | 2005/020861 A1 | 3/2005 |
| WO | 2005/023150 A2 | 3/2005 |
| WO | WO-2006007739 A1 | 1/2006 |
| WO | 2006/116850 A1 | 11/2006 |
| WO | 2007/118177 A2 | 10/2007 |
| WO | 2007/118179 A2 | 10/2007 |
| WO | WO-2007124130 A2 | 11/2007 |

OTHER PUBLICATIONS

[No author listed] Memory Staple: Surgical Technique, Controlled compression for fusion. DePuy Orthopaedics, Inc. 2006. 16 pages.
International Search Report and Written Opinion for Application No. PCT/US2012/51836, issued Jan. 23, 2013. (15 pages).
Chinese Notice of Allowance for Application No. 201280042448.9, issued on Jan. 7, 2016 (5 pages).
Australian Office Action for Application No. 2012300452, issued Mar. 4, 2016 (4 pages).
Supplementary Partial Search Report issued Sep. 8, 2015, for European Application No. 12828175.5 (7 pages).
Extended European Search Report issued Jan. 5, 2016, for European Application No. 12828175.5 (11 pages).
Chinese Office Action for Application No. 201610147641.9, mailed Mar. 1, 2017 (22 pages).

(56) References Cited

OTHER PUBLICATIONS

Japanese Office Action for Application No. 2014-528454, issued Feb. 14, 2017 (7 pages).

* cited by examiner

DEVICES AND METHODS FOR CERVICAL LATERAL FIXATION

FIELD

The present disclosure relates to devices and methods for treating the cervical region of the spine, and more particularly relates to devices for and methods of performing treatments to that region from a lateral or posterior-lateral location of a subject.

BACKGROUND

The human spine includes vertebrae and joints that work together to protect the spinal cord from injury during motion and activity. The spinal cord generally includes nerve elements that travel from the brain to other portions of the body so that the brain can command the other portions of the body to respond in particular manners based on bioelectrical and biochemical signals transmitted by the brain, through the spinal cord, and ultimately to the portion of the body being commanded by the brain.

The spine itself is typically grouped into three sections: the cervical spine (which is in the region of the neck), the thoracic spine (which is in the region of the middle of the back), and the lumbar spine (which is in the region of the lower back). The cervical spine, which is typically considered to include the C1-C7 vertebrae, is known as a sensitive area of the spine that requires caution when performing surgical procedures in the area. The bones in this area are small and delicate. Surgical procedures performed in that area can include procedures for treating spinal stenosis and nerve root compression. Procedures performed in the cervical region of the spine have typically involved approaching the region from an anterior location of a subject, and care must be taken to avoid damage to the spinal cord or other anatomical structures located in that vicinity, such as the Carotid artery and the Jugular vein.

It would be desirable to provide devices and methods that can be used for treatment of the cervical region of the spine from locations that are considered lateral or posterior-lateral of a subject while still allowing appropriate care to be taken to avoid damage to anatomical structures in that region.

SUMMARY

Devices and methods are generally provided for treatment of the cervical spine from a lateral or posterior-lateral location of a subject. In one embodiment a spinal implant includes an elongate cage member having a distal insertion end and a proximal anchoring end and a plate member appended to the cage member in proximity to the proximal anchoring end. The cage member can be oriented in a first direction. An external surface of the cage member extends between the proximal and distal ends of the cage member, which can be defined by a superior surface, an inferior surface, an anterior wall, and a posterior wall. The cage member can have a hollow interior and a plurality of openings formed in the external surface. The plate member can have a long axis that is generally perpendicular to the first direction of the cage member. The plate member can have a curve along a short axis of the plate member, and the plate member can be asymmetric with respect to the long axis of the cage member. For example, the plate member can be oriented with respect to the elongate cage member such that a midpoint of the plate member is disposed anterior to the long axis of the cage member.

In one embodiment the superior surface of the cage member is generally concave while the inferior surface of the cage member is generally convex. The distal insertion end of the cage member can have an asymmetrical, bulleted shape. Such a shape can result from a curve of the inferior surface being greater than a curve of the superior surface, and, as a result, the distal insertion end is biased toward a superior direction. The posterior and anterior walls of the cage member can also include a curve. The posterior wall can have a curve that is generally concave; the anterior wall can have a curve that is generally convex. In one embodiment a radius of the curve of the anterior wall of the cage member can be substantially the same as a radius of the curve of the short axis of the plate member.

The cage member can be configured to be delivered to a cervical spine through a lateral surgical approach. Additionally, the superior and/or inferior surfaces of the cage member can include one or more surface features that are configured to prevent migration of the implant. The plate member can include a plurality of wings. The wings can be configured to engage a surface by way of attachment features. In one embodiment an angle formed between the short axis of the plate member and the plane of the cage member is less than 90 degrees. For example, the angle between the short axis and the cage member plane can be in the range of about 35 degrees to about 80 degrees. The implant itself can include one or more bores configured to receive a screw to aid in securing the implant to bone.

In another exemplary embodiment of a spinal implant, the implant includes an elongate cage member having distal and proximal ends, the distal end having an asymmetrical, bulleted shape. The shape is such that a curve of an inferior surface of the cage member is greater than a curve of a superior surface of the cage member. As a result, the distal end is biased towards a superior direction. An external surface of the cage member extends between the ends of the cage member and is defined by the aforementioned superior surface, which is generally concave, and the aforementioned inferior surface, which is generally convex, as well as an anterior wall and a posterior wall. The cage member can have a hollow interior and a plurality of openings formed in its external surface.

In one embodiment the cage member can also include a plate member that is integrally formed on the cage member in proximity to the proximal end of the cage member. The plate member can have a long axis that is generally perpendicular to a long axis of the cage member. The plate member can also have a curve along a short axis of the plate member. In one embodiment the plate member can be asymmetric with respect to the long axis of the cage member. In another embodiment the plate member can be oriented with respect to the cage member such that a midpoint of the plate member is disposed anterior to the long axis of the cage member. In still another embodiment an angle formed between the short axis of the plate member and the long axis of the cage member is less than 90 degrees. For example, the angle between the two axes can be in the range of about 35 degrees to about 80 degrees.

The cage member can be configured to be laterally delivered to a cervical spine. Additionally, the superior and/or inferior surface of the cage member can include one or more surface features configured to prevent migration of the implant. The posterior and anterior walls of the cage member can include a curve. The posterior wall can have a curve that is generally concave; the anterior wall can have a curve that is generally convex. In one embodiment a radius of the curve of the anterior wall of the cage member can be substantially the same as a radius of the curve of the short axis of the plate member. The implant itself can include one or more bores configured to receive an anchor member, such as a screw, to aid in securing the implant to bone.

In one exemplary embodiment of a method for treating a cervical spine, the method includes inserting a spinal implant between two adjacent vertebrae of a cervical spine and fixing a plate member of the spinal implant such that a midpoint of the plate member is disposed anterior to a long axis of the spinal implant. The insertion of the implant can occur from a position that is lateral or posterior-lateral to the cervical spine. For example, in one instance, insertion can occur anywhere between a position that is substantially perpendicular to a plane extending through a subject that substantially bisects the subject into two substantially equal halves and a position that is substantially 45 degrees in a posterior-direction to the plane. The spinal implant can include a cage member. The plate member can be fixed relative to the cage member. In one embodiment the plate member can be oriented with respect to the cage member such that a midpoint of the plate member is disposed anterior to a long axis of the cage member.

In another exemplary embodiment of an implantable spinal fixation device, the device can include an elongate rod member and at least two mounting eyelets. The first mounting eyelet can be formed on the elongate rod member in proximity to a distal end of the rod member. The second mounting eyelet can also be formed on the elongate rod member, remote from the first mounting eyelet. An opening can be formed in each of the first and second mounting eyelets. The first mounting eyelet can have a central axis that intersects a longitudinal axis of the rod member or a central axis that is offset from a longitudinal axis of the rod member. Likewise, the second mounting eyelet can have a central axis that intersects a longitudinal axis of the rod member or a central axis that is offset from a longitudinal axis of the rod member. Thus, in one embodiment both a central axis of the first mounting eyelet and a central axis of the second mounting eyelet can intersect a longitudinal axis of the rod member. In another embodiment a central axis of the first mounting eyelet can intersect a longitudinal axis of the rod member while a central axis of the second mounting eyelet can be offset from the longitudinal axis of the rod member. In still another embodiment both a central axis of the first mounting eyelet and a central axis of the second mounting eyelet can be offset from the longitudinal axis of the rod member.

The mounting eyelets can have a variety of locations with respect to each other and with respect to proximal and distal ends of the rod member. For example, the second mounting eyelet can be in proximity to a proximal end of the rod member. By way of further example, the first mounting eyelet can be at the distal end of the elongate rod member. A length of the elongate rod member can be adjustable between the first and second mounting eyelets. In one embodiment a first segment of the elongate rod member can be configured to slide with respect to a second segment of the elongate rod member. A diameter of the second segment can be larger than a diameter of the first segment and the second segment can be configured to slidingly receive the second segment. In another embodiment the elongate rod member can include one or more locking members disposed between first and second segments of the elongate rod member. The one or more locking members can be configured to selectively move and lock the segments to adjust a length of the elongate rod member between the first and second mounting eyelets.

The rod member can have a pre-determined curve, and in one embodiment the curve can be complementary of a curve of a spine. Alternatively, the rod member can be substantially thin and flat. The rod member can also be bendable. In one embodiment the rod member can include a plurality of vertices disposed between the first and second mounting eyelets. For example, a first vertex can be disposed on one side of a longitudinal axis of the rod member and a second vertex can be disposed on an opposite side of the longitudinal axis of the rod member. The openings of the first and second mounting eyelets can be configured to receive a screw therein such that a central axis disposed through a screw received by the first mounting eyelet is in a non-parallel position with respect to a central axis disposed through a screw received by the second mounting eyelet.

In another exemplary embodiment of a method for treating a cervical spine, the method includes inserting a rod member having first and second mounting eyelets through an opening proximate to a cervical spine, attaching the first mounting eyelet to a first vertebra in a cervical spine, and attaching a second mounting eyelet to a second vertebra in a cervical spine. The opening can be located lateral or posterior-lateral to the cervical spine. Either or both of the mounting eyelets can be offset from a longitudinal axis of the rod member. In one embodiment the method can include adjusting a length of the rod member between the first and second mounting eyelets. The method can also include adjusting a shape of the rod member between the first and second mounting eyelets. Further, a second rod member can be inserted through the opening that is proximate to the cervical spine. The second rod member can be positioned such that the second rod member is substantially parallel to the first rod member. The second rod member can then be attached to vertebrae in the cervical spine, for instance by attaching a first mounting eyelet of the second rod member to one vertebra and attaching a second mounting eyelet of the second rod member to another vertebra.

BRIEF DESCRIPTION OF DRAWINGS

This invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Figure 1:
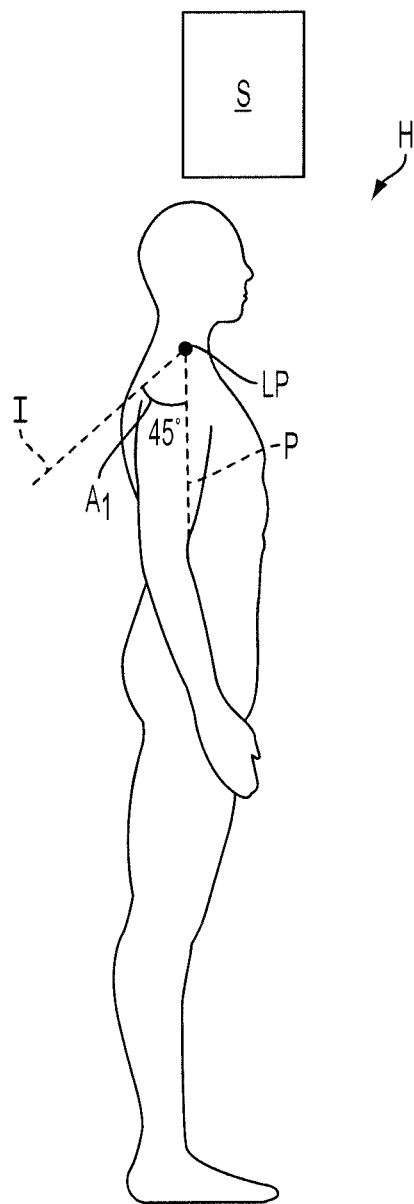
FIG. 1 is a schematic view of a human subject illustrating an exemplary location for an incision in which implants of the nature disclosed herein can be inserted into the subject.

Devices and methods for fixing and/or stabilizing a location of bones in the cervical region of the spine are generally provided. The fixation approach disclosed herein allows for delivery of spinal implants in a manner not typically relied upon for spinal fixation procedures. In particular, as illustrated in FIG. 1, the devices and methods allow for spinal implants to be implanted in a subject H from a lateral point of access LP. Implants can be inserted through the lateral point of access at an angle that is substantially perpendicular to a sagittal plane S. Alternatively, implants can be inserted from a posterior-lateral location. For example, a point of access can be disposed in a direction that is posterior of the lateral point of access LP. By way of further example, an angle of insertion defined by a plane I can be non-perpendicular to the sagittal plane S, preferably at an angle that is posterior to a plane P that is substantially perpendicular to the sagittal plane S. As shown, in one exemplary embodiment an angle $A_1$ formed between the plane P and the insertion plane I is approximately 45 degrees in a posterior-direction to the plane P. The angle of insertion $A_1$ can occur at any access point, including the lateral point of access LP as shown, or at a point of access that is posterior to the lateral point of access LP. The lateral or posterior-lateral approach can be achieved in view of the present devices and methods without creating a substantial risk of causing undesirable damage to this sensitive area, which contains anatomical structures including the Carotid artery and Jugular vein.

A variety of devices and methods are disclosed herein. Some devices include spinal implants configured to be disposed between adjacent vertebrae. Other devices include spinal fixation elements that can be configured to extend from one vertebra to one or more additional vertebrae, even if those vertebrae are not adjacent. The methods include surgical techniques that allow implants to be disposed through a small incision that is positioned lateral or posterior-lateral of a subject being treated. In the present disclosure, like-numbered components of the embodiments generally have similar features, and thus within a particular embodiment each feature of each like-numbered component is not necessarily fully elaborated upon. Further, to the extent that linear or circular dimensions are used in the description of the disclosed devices and methods, such dimensions are not intended to limit the types of shapes that can be used in conjunction with such devices and methods. A person skilled in the art will recognize that an equivalent to such linear and circular dimensions can easily be determined for any geometric shape. Sizes and shapes of each of devices, and the components thereof, can depend at least on the anatomy of the subject in which the devices will be used and the size and shape of components with which the devices will be used.

Lateral Anterior Fusion Cage

FIGS. 2A-2F illustrate one exemplary embodiment of a spinal implant 10, which is in the form of a lateral anterior fusion cage 20. As explained below, the disclosed lateral anterior fusion cage has a design that lends itself to implantation in a subject's spine via a lateral or posterior-lateral surgical approach. Moreover, the design is such that the implant maximizes the footprint of the implant component that is to reside between adjacent vertebral bodies while providing a large internal volume, which can serve as a graft chamber. As described below, the implant is asymmetric about a long axis of its cage. For example, a plate member 50 is asymmetric about a long axis $L_1$ of the cage member 20 such that the plate member is not equally sized and shaped on both sides of the long axis $L_1$. In one illustrated embodiment, the plate member 50 is entirely on one side of the long axis $L_1$.

In the description of the lateral anterior fusion cage that follows, reference is made to orientation of the device when in a condition in which it is implanted within a subject. That is, with the cage member 20 disposed between adjacent vertebral bodies and the plate member (if present) attached to a lateral wall of the vertebral bodies. In one exemplary embodiment the cage member can closely match an anatomy of a central to posterior portion of a vertebral body and can therefore be disposed in the central to posterior portion of the cervical region of the spine.

As illustrated, the implant 10 can include both an elongate cage member 20 that is configured to be inserted between adjacent vertebrae and an optional plate member 50 that can be appended to the cage member 20 and that can be used to assist in securing the implant 10 at a desired location, such as on a lateral wall of one or more vertebral bodies. The cage member 20 is generally oriented in a transverse plane of the body when implanted, extending laterally to medially between its proximal and distal ends 20p, 20d. The appended plate member 50, when implanted, generally extends in the caudal to cephalad direction. The cage member can be regarded to be of a generally rectangular shape in that it is elongate and has four sides. However, as explained below, each of the sides can be non-linear in shape. As a result, in some embodiments, the cage member 20 can be described as having a generally banana-like or canoe-like shape.

Figure 2A:
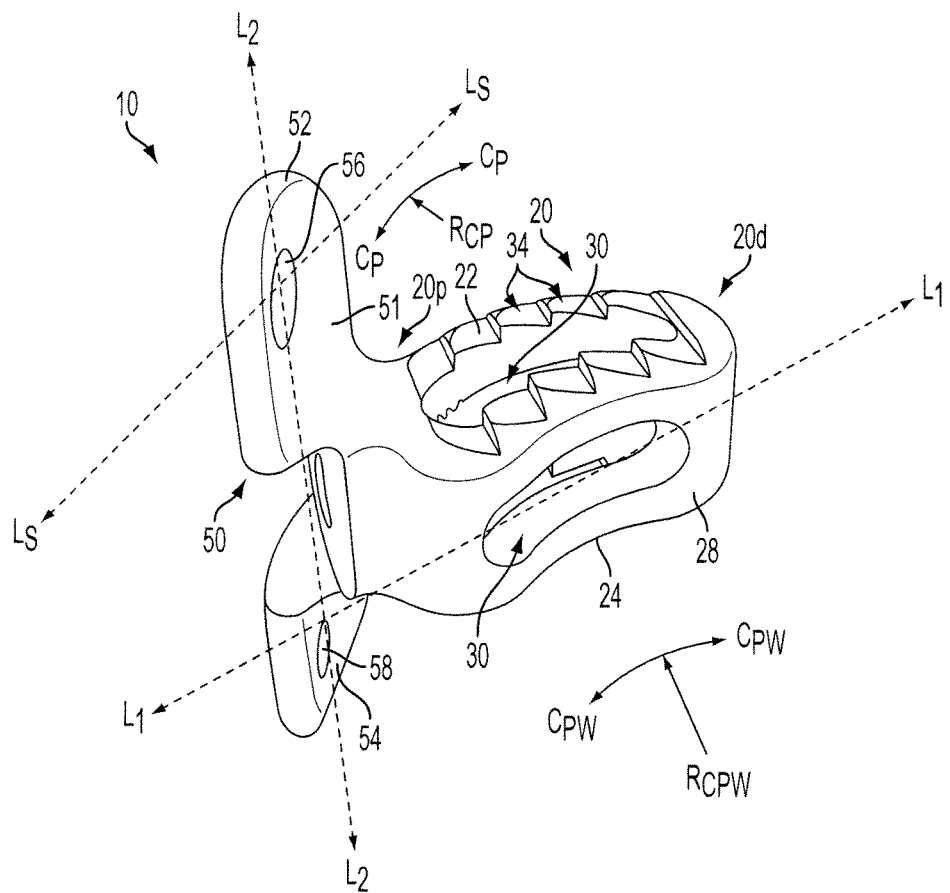
FIG. 2A is a perspective view of an anterior and superior portion of one exemplary embodiment of a spinal implant that includes a cage member and a plate member.
Figure 2B:
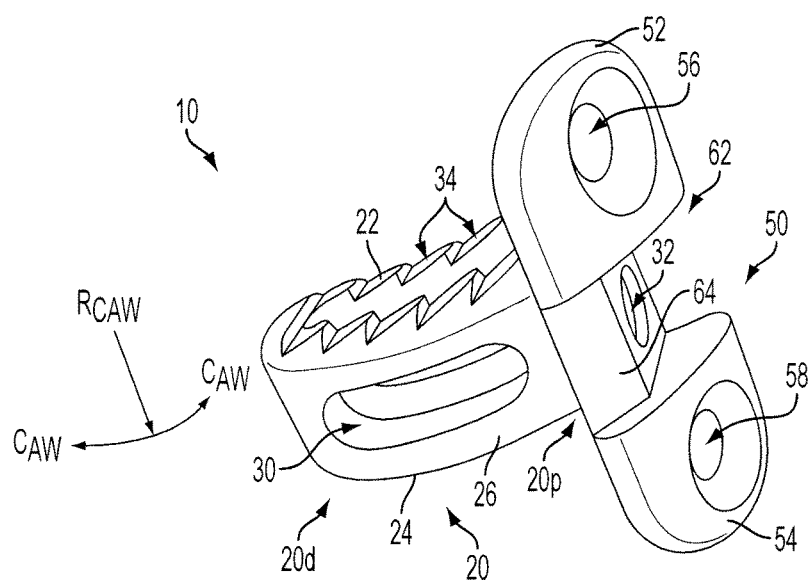
FIG. 2B is a perspective view of a posterior and superior portion of the spinal implant of FIG. 2A.
Figure 2C:
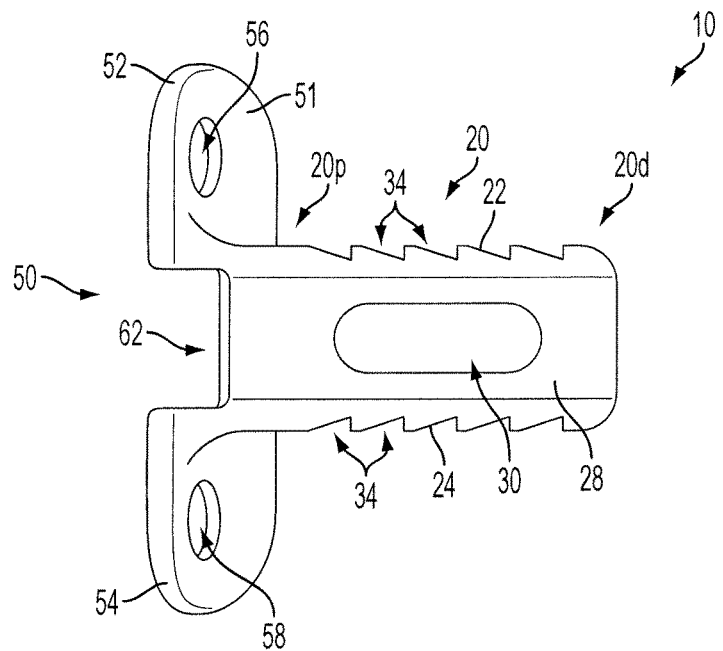
FIG. 2C is a perspective view of a posterior portion of the spinal implant of FIG. 2A.
Figure 2D:
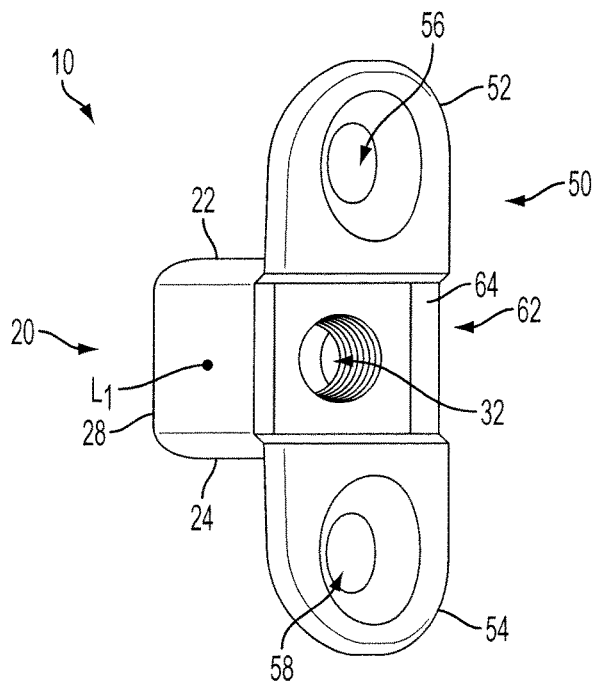
FIG. 2D is a perspective view of a proximal end of the spinal implant of FIG. 2A.
Figure 2E:
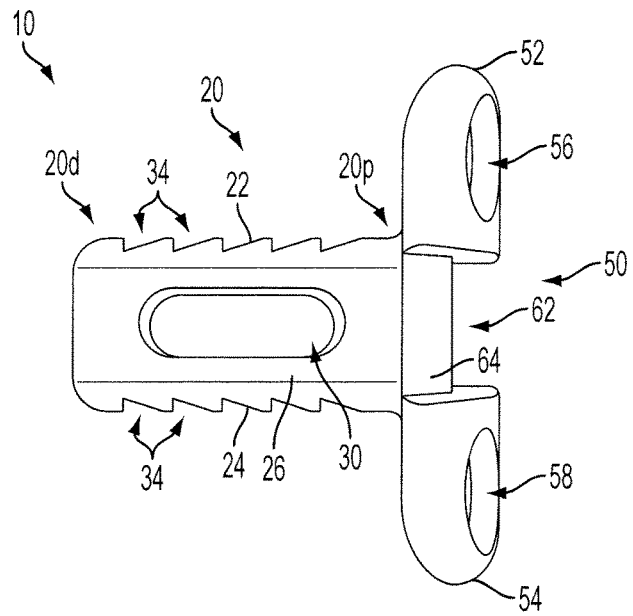
FIG. 2E is a perspective view of an anterior portion of the spinal implant of FIG. 2A.
Figure 2F:
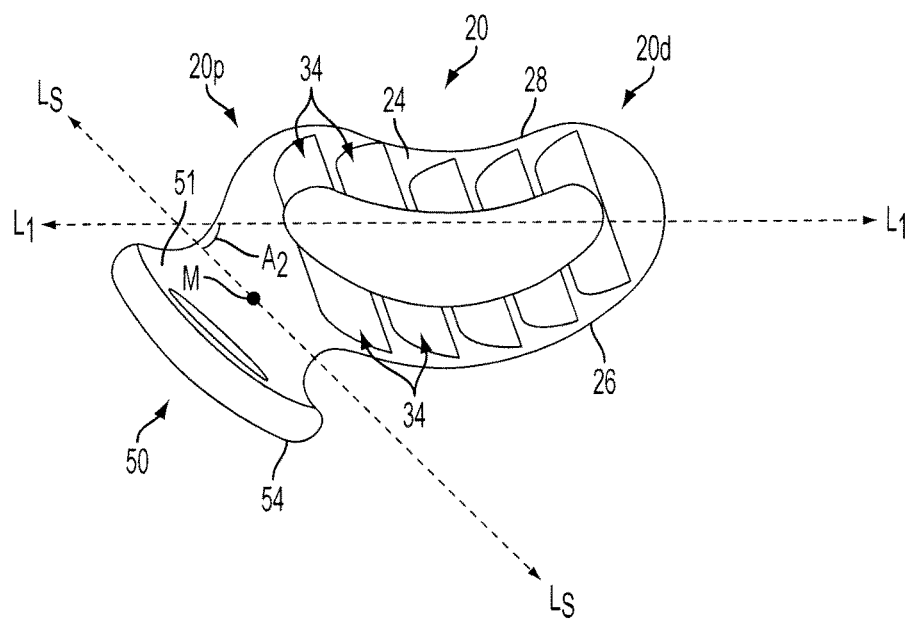
FIG. 2F is a perspective view of an inferior portion of the spinal implant of FIG. 2A.

As shown in FIGS. 2A and 2F, the cage member 20 can be elongate, and for reference purposes can be described as being oriented along a longitudinal axis $L_1$ in the transverse plane. The cage member 20 can also be described as having an external surface that extends between the proximal and distal ends 20p, 20d, which is defined by a superior surface 22, an inferior surface 24, an anterior wall 26, and a posterior wall 28. One or more relief slits or openings 30 can be formed in the external surface to, optionally, permit bone graft and/or bone growth-promoting material to be disposed therein, and thus facilitate integration of the implant within a subject.

The distal end 20d of the cage member 20 can be configured for insertion between vertebral bodies of a subject and to optimize stable fixation within the subject. As shown, the distal end 20d is of a rounded or bullet-shaped nature. Generally, the distal end 20d serves as the leading edge of the implant 10 when disposing the implant 10 through an incision and into an intervertebral implantation site. The proximal end 20p of the cage member 20, on the other hand, is the trailing end of the spinal implant 10 and can include features adapted for anchoring the implant to a vertebral body, such as the plate member 50. As shown, the proximal end 20p can also tend to have rounded edges. The proximal end 20p can also include one or more features that enable the implant to be mated to an insertion instrument. An example of such a feature is threaded bore 32 (FIG. 2D).

The surfaces 22, 24, 26, and 28 that define the external surface of the cage member 20 are sized and shaped in a manner that optimizes the placement and fixation of implant 10 between vertebral bodies in the cervical region of the spine, and particularly when the implant is positioned within the spine through lateral or posterior-lateral access. In the illustrated embodiment the surfaces 22, 24, 26, and 28 are configured to be complementary to the shape of the vertebral bodies at the site of implantation. For example, the anterior wall 26 is curved and is configured to be disposed at or proximate to an anterior portion of the vertebral body, while the posterior wall 28 is also curved and is configured to be disposed at or proximate to a posterior portion of the vertebral body. As illustrated, a curve $C_{AW}$ of the anterior wall 26 is generally convex (FIG. 2B) while a curve $C_{PW}$ of the posterior wall 28 is generally concave (FIG. 2A). Radii $R_{CAW}$, $R_{CPW}$ of the curves $C_{AW}$, $C_{PW}$ can vary depending on the size of the implant. Generally, however, the radii $R_{CAW}$, $R_{CPW}$ are substantially the same and can be in the range of about 7 millimeters to about 25 millimeters. In one embodiment the radii $R_{CAW}$, $R_{CPW}$ can be about 10 millimeters.

Figure 3A:
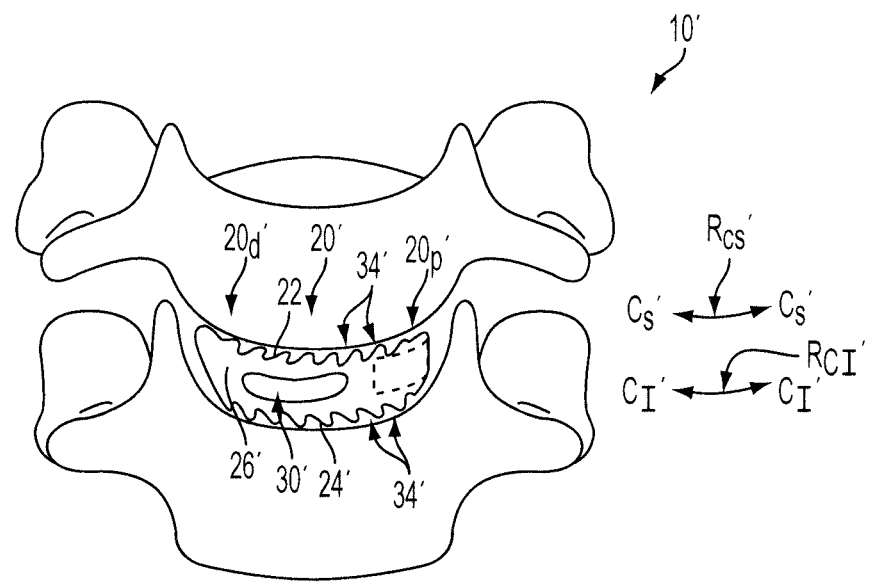
FIG. 3A is an anterior view of one exemplary embodiment of a spinal implant that includes a cage member, the implant being disposed between two adjacent vertebrae.

In the embodiment illustrated in FIGS. 2A-2F, the superior and inferior surfaces 22 and 24 are substantially linear. However, in other embodiments, for example the embodiment illustrated in FIG. 3A, an implant can have superior and inferior surfaces that are generally curved. The implant 10' shown in FIG. 3A can include a cage member 20' with an external surface that includes a superior surface 22', an inferior surface 24', and an anterior wall 26' that are each generally curved. The external surface can also include a posterior wall (not shown), which can also be generally curved. Similar to what is described in FIGS. 2A-2F, a curve $C_{AW}'$ of the anterior wall 26' is generally convex. Further, a curve $C_S'$ of the superior surface 22' is generally concave while a curve $C_I'$ of the inferior surface 24' is generally convex. The radii $R_{CS}'$, $R_{CI}'$ of the curves $C_S'$, $C_I'$ can vary depending on the size of the implant, and can be in the range of about 10 millimeters to about 30 millimeters. In one embodiment the radii $R_{CS}'$, $R_{CI}'$ can be about 18 millimeters. While in some instances the radii $R_{CS}'$, $R_{CI}'$ can be substantially the same, in the illustrated embodiment the radii $R_{CS}'$, $R_{CI}'$ are different, with the inferior surface having a greater degree of curvature than the superior surface. When the radius $R_{CI}'$ of the inferior surface 24' is greater than the radius $R_{CS}'$ of the superior surface 22', as shown in FIG. 3A, the cage member 20' has an asymmetrically-curved, bullet-shaped distal end 20d' that can be described as having a generally banana-like or canoe-like shape.

The external surface of the implant 10, 10' may include surface features that prevent migration and assist in maintaining a location of the spinal implant. For example, in the illustrated embodiments the superior and inferior surfaces 22, 22' and 24, 24' include a plurality of ridges 34, 34'. Ridges 34, 34' can take a variety of forms, as one skilled in the art will appreciate. However, in one embodiment the ridges can be of a triangular cross section with the apex at a distal position and a one-way directional slant as shown for example in FIGS. 2C and 2E. The directional slant allows insertion of the implant but resists its removal. Other surface features known to those skilled in the art can also be provided without departing from the spirit of the invention.

The external surface of the implant 10, 10' may also include a plurality of relief slits or openings 30, 30' to permit access to an internal volume within the implant. As those skilled in the art will appreciate, the internal volume may be packed with bone graft and/or bone growth-promoting materials to enhance and expedite integration of the implant into a subject's body. While in the illustrated embodiment of FIGS. 2A-2F each of the superior surface 22, inferior surface 24, anterior wall 26, and posterior wall 28 including openings 30, in other embodiments only some of the surfaces or walls may include an opening(s), or even none of the surfaces or walls may include openings. Similarly, more than one opening can be formed on one or more sides of the external surface.

The presence of a plate member 50 part of the implant 10 is optional. FIG. 3A illustrates an embodiment in which the implant 10' of FIG. 3A does not include a plate member. Although a plate member can assist in securing the implant at a desired location between vertebral bodies, the shape of the implant itself can provide sufficiently secure placement of the implant. For example, the banana-like shape and asymmetrical curve of the implant 10' enables stable placement of the implant 10' without the need for a plate member.

FIGS. 2A-2F illustrate an implant 10 that does include a plate member 50 disposed in proximity to the proximal end 20p of the cage member 20. While in the illustrated embodiment the plate member 50 is integrally formed with the proximal end 20p, it can be appended to the proximal end 20p in other ways known to those having skill in the art. By way of non-limiting examples, a plate member can be slidingly coupled to a cage member or removably and replaceably coupled to a cage member.

The plate member 50 generally extends in a direction that is opposite to that of the elongate direction of the cage member 20. As shown in FIG. 2A, while the cage member 20 extends along a long axis $L_1$, the plate member 50 extends in a long axis $L_2$ in a direction that is generally perpendicular to the direction of the longitudinal axis $L_1$. The plate member 50 can also be asymmetric with respect to the long axis $L_1$. In the illustrated embodiment, the plate member 50 is entirely on one side of the long axis $L_1$. In one embodiment the orientation of the plate member 50 and the cage member 20 is such that when the cage member is parallel to the transverse axis of a subject's body, the plate member is not parallel to the sagittal plane. Rather, the plate member is anteriorly offset such that it is angled with respect to the sagittal plane. Such a construction enables the plate member to be mounted to an anterior portion of the lateral wall of a vertebral body. As a result of the plate member 50 being biased towards an anterior side of the spinal implant 10, a midpoint M of the plate member 50 is disposed anterior to the long axis $L_1$ of the cage member 20 as shown in FIG. 2F. Accordingly, an angle $A_2$ formed by orientation of the plate member 50 and the orientation of the cage member 20 (illustrated by the long axis $L_1$ of the cage member 20 and the short axis $L_S$ of the plate member 50) can be less than 90 degrees (FIG. 2F), and is generally in the range of about 35 to about 80 degrees. In one embodiment the angle $A_2$ can be about 47 degrees. A configuration in which the midpoint M of the plate member 50 is disposed anterior to the long axis $L_1$ of the cage member 20 can allow the plate member 50 to mount on a proximal lateral wall of the spine, anterior to the Carotid artery, within the C3 to C7 vertebrae range of the spine.

The plate member 50 is also curved along its short axis $L_S$, as shown in FIG. 2A, to complement the shape of the lateral walls of the vertebrae upon which the plate member will mount. As shown in FIG. 2A, an internal surface 51 of the plate member 50 has a concave shape. Although a radius $R_{CP}$ of a curve $C_P$ of the plate member 50 can vary, it is generally in the range of about 10 millimeters to about 30 millimeters. In one embodiment the radius $R_{cp}$ is about 15 millimeters.

One skilled in the art will appreciate that the plate member 50 can have a variety of shapes and sizes. In the illustrated embodiment the plate member 50 is generally rectangular and it extends in both the superior and inferior directions of the cage member 20. Alternatively, it can extend in a single direction such that it mates to only one of the two adjacent vertebral bodies. The plate member 50 can include one or more mating features to assist in mating the plate member 50 to vertebrae. As shown, the mating features can include a first bore 56 in a first wing 52 of the plate member 50 and a second bore 58 in a second wing 54 of the plate member 50. Anchor members, such as screws complementary to the bores 56, 58, can then be used to secure the plate member 50, and thus the spinal implant 10.

Mating features configured to be engaged by an insertion instrument can also be provided as part of the plate member. In the illustrated embodiment a threaded bore 32 is provided as such a mating feature. As shown, the threaded bore 32 of the plate member 50 can be engaged by an installation instrument (not shown) to assist in the insertion of the implant 10. The illustrated embodiment also includes further features for receiving insertion instruments. For example, a receiving groove 62 is provided that provides an indentation between the first and second wings 52 and 54 of the plate member 50. As illustrated, the receiving groove 62 includes a chamfer 64 that can be formed to be complementary to a shape of an insertion instrument.

In some embodiments the plate member can include one or more anti-migration features. For example, one or more spikes, ridges, or other bone-engaging features can be disposed on the internal surface 51 of the plate member 50. These features can be configured to engage an adjacent vertebral body to assist in maintaining the plate, and thereby the implant, at a desired location.

Figure 3B:
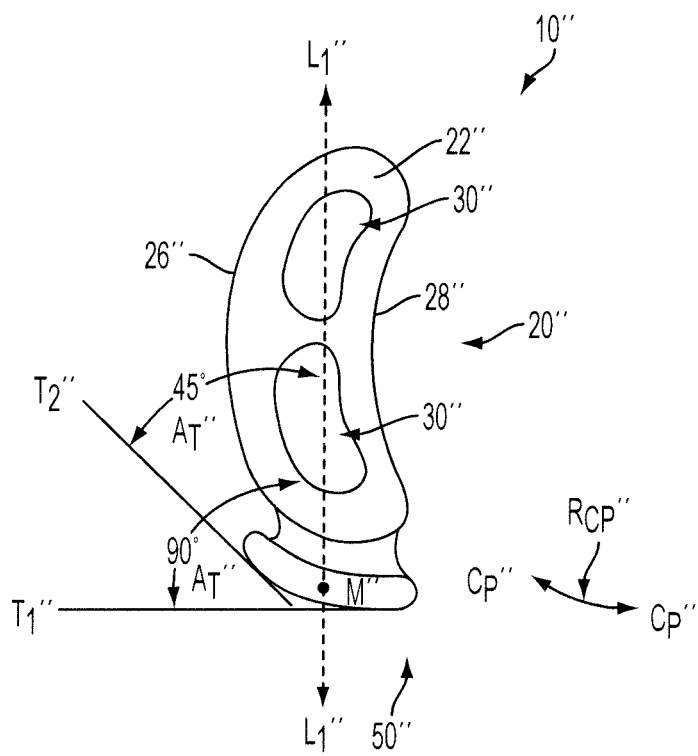
FIG. 3B is a top view of another exemplary embodiment of a spinal implant that includes a cage member and a plate member.

FIG. 3B illustrates another embodiment of a spinal implant 10" having both a cage member 20" and a plate member 50". The external surface of the cage member 20" is generally similar to the cage members 20 and 20', although as shown the superior surface 22" includes more than one relief slit or opening 30" formed therein. In one embodiment, the plate member 50" is asymmetric with respect to a long axis $L_1$" of the cage member 20". That is, the plate member 50" is not equally sized and shaped on both sides of the long axis $L_1$". A curve $C_P$" of the external surface of the plate member changes as the curve $C_P$" moves from the posterior wall 28" to the anterior wall 26". In one embodiment a radius $R_{CP}$" of curvature of the curve $C_P$" can be approximately in the range of about 5 millimeters to about 30 millimeters proximate to the posterior wall 28" and approximately in the range of about 5 millimeters to about 45 millimeters proximate to the anterior wall 26". In one embodiment the radius $R_{CP}$" is about 5 millimeters proximate to the posterior wall 28" and about 20 millimeters proximate to the anterior wall 26".

In the illustrated embodiment, the midpoint M" of the plate member 50" is approximately aligned with the long axis $L_1$" of the cage member 20", although it can be offset anteriorly as described herein. Successive tangent lines, as shown lines $T_1$" and $T_2$", are asymmetric to the long axis $L_1$". For example, as a tangent line of the plate member 50" moves successively from the posterior wall 28" to the anterior wall 26", an angle $A_T$" formed by the tangent line and the long axis $L_1$" decreases. In one embodiment the angle $A_T$" decreases from an initial point (i.e., posteriormost) adjacent to the posterior wall 28" in which the angle $A_T$" is in the range of about 80 degrees to about 95 degrees, to a point adjacent to the anterior wall 26" in which the angle $A_T$" is in the range of about 35 degrees to about 50 degrees. In the illustrated embodiment the angle $A_T$" for the tangent line $T_1$" is about 90 degrees and the angle $A_T$" for the tangent line $T_2$" is about 45 degrees.

Although the spinal implant 10 is described as having two components, a cage member 20 and a plate member 50, each being generally rectangular in shape and having particular curvatures that can be advantageous in certain instances, a variety of other shapes and curves can also be used in such cervical spine techniques without departing from the spirit of the invention. Accordingly, although the cage member is described as being of a generally rectangular shape and having walls and surfaces that are convex or concave, any walls and surfaces of the cage member can be virtually any shape, including generally flat, convex, or concave. Likewise, the cage member can take the form of a variety of other shapes. Similarly, plate members can have a variety of configurations. Non-limiting examples of configurations of plate members that can be used in accordance with the present invention are provided in FIGS. 4A-4F.

Figure 4A:
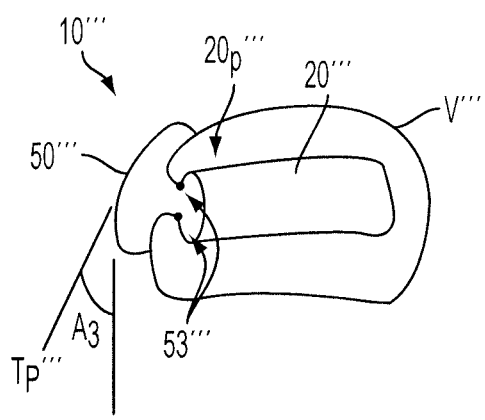
FIG. 4A is a top view of an exemplary embodiment of a spinal implant that includes a bend zone between a cage member and a plate member, and having a vertebral body disposed therebelow.
Figure 4B:
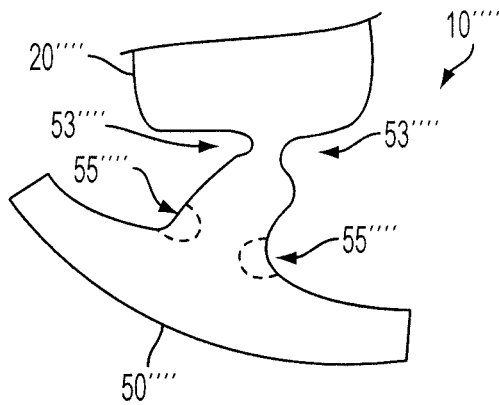
FIG. 4B is a top view of another exemplary embodiment of a spinal implant that includes multiple bend zones between a cage member and a plate member.

As shown in FIGS. 4A and 4B, some embodiments of implants 10''', 10'''' can include bend zones 53''', 53'''' associated with the connection between cage and plate members 20''', 20'''' and 50''', 50''''. The bend zones 53''', 53'''' provide a level of flexibility or adjustability between the plate member 50''', 50'''' and the cage member 20''', 20'''' and can allow the plate member 50''', 50'''' to more accurately conform to an anatomy of a vertebral body, as shown in FIG. 4A with respect to the vertebral body V'''. An angle $A_3$ formed by a proximal end 20p''' of the cage member 20''' and a tangent $T_P$''' of the plate member can be in the range of about 10 degrees to about 50 degrees. In one embodiment the angle $A_3$ is in the range of about 30 degrees to about 45 degrees. As shown in FIG. 4B, bend zones 55'''' can also be formed within the plate member 50'''' itself, providing further flexibility and conformity to a desired surgical location.

Figure 4C:
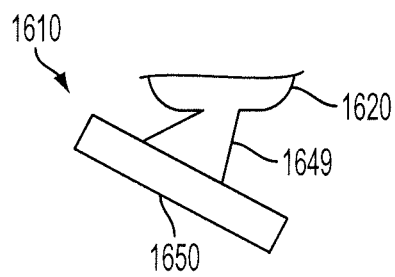
FIG. 4C is a top view of yet another exemplary embodiment of a spinal implant in which the plate member appended to the cage member is substantially flat.
Figure 4D:
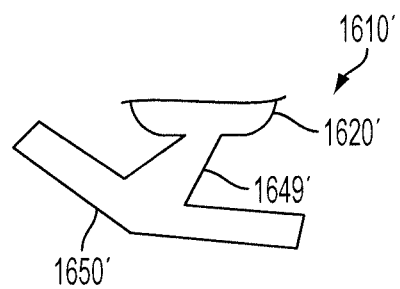
FIG. 4D is a top view of still another exemplary embodiment of a spinal implant in which the plate member appended to the cage member is generally V-shaped.
Figure 4E:
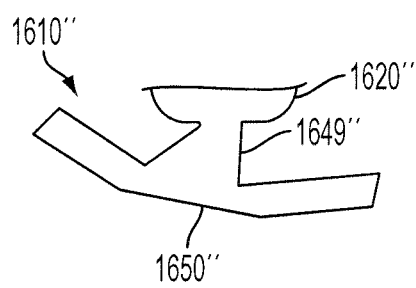
FIG. 4E is a top view of another exemplary embodiment of a spinal implant in which the plate member appended to the cage member is generally U-shaped.
Figure 4F:
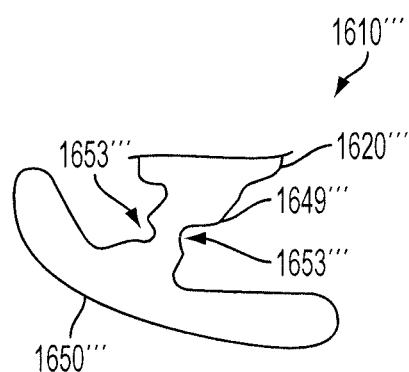
FIG. 4F is a top view of yet another exemplary embodiment of a spinal implant in which the plate member appended to the age member is generally U-shaped and in which bend zones are located between the cage member and the plate member.

As discussed above, the plate member can include a variety of different shapes and sizes. Non-limiting examples of plate member shapes are shown in FIGS. 4C-4F. A plate member 1650 of an implant 1610 shown in FIG. 4C is substantially flat and mates to a cage member 1620 by way of a triangular coupling portion 1649. A plate member 1650' of an implant 1610' in FIG. 4D is substantially V-shaped and is mounted to a cage member 1620' by way of a polygonal coupling portion 1649'. A plate member 1650'' of an implant 1610'' shown in FIG. 4E is substantially U-shaped and is mounted to a cage member 1620'' by way of a polygonal coupling portion 1649''. A plate member 1650''' of an implant 1610''' shown in FIG. 4F is substantially curved and is mounted to a cage member 1620''' by a flexible coupling portion 1649'''. Any or all of these embodiments can include bend zones, like the bend zones 1653''' of the implant 1610''' of FIG. 4F, and can include characteristics and features of the other implants described herein.

Figure 5A:
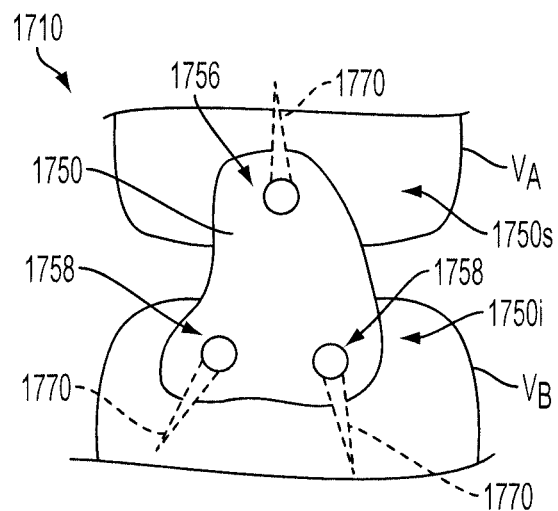
FIG. 5A is an anterior view of an exemplary embodiment of plate member of a spinal implant.
Figure 5B:
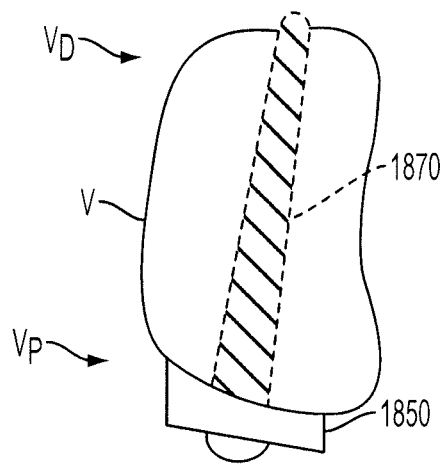
FIG. 5B is a top schematic view of an exemplary embodiment of a fixation element being disposed in a spinal implant.

A proximal end of a plate member can also have a variety of shapes in addition to the generally rectangular shape illustrated in FIGS. 2A-2F. In the embodiment shown in FIG. 5A, for example, a proximal end 1750p of a plate member 1750 of an implant 1710 can be generally triangular. As shown, a superior end 1750s of the plate member 1750 includes one bore 1756 while an inferior end 1750i includes two bores 1758. Anchoring elements 1770 that are configured to be disposed in the bore 1756, 1758, can engage adjacent vertebrae $V_A$ and $V_B$. In embodiments in which more than one bore is associated with the same vertebral body, such as the bores 1758, the bores 1758 can be configured in a manner such that the anchoring elements 1770 disposed therein are non-parallel. Further, multiple points of fixation can be achieved by a single anchoring element. For example, as shown in FIG. 5B, an anchoring element 1870 can cause bilateral fixation by being fixed through a plate member 1850 at both a proximal end $V_P$ of a vertebral body V, i.e., the first cortex, and a distal end $V_D$ of a vertebral body V, i.e., the cortical wall, the fixation element 1870 terminating past the cortical wall of the same vertebral body V.

One skilled in the art will appreciate that the implant can be made from any number of biologically-compatible materials used to form spinal implants, including materials that are partially or fully bioresorbable. Exemplary materials include titanium, titanium alloys, titanium mesh, polyether ether ketone (PEEK), reinforced PEEK, and Nitinol®.

In a method of implanting the lateral anterior fusion cages illustrated and described herein, an incision or delivery aperture in the range of approximately 25 millimeters to approximately 35 millimeters can be formed in an area near the cervical region of the spine. In an exemplary embodiment, the incision is formed at a location that is lateral or posterior-lateral of a subject, as illustrated in FIG. 1. The devices and methods allow for spinal implants to be implanted in a subject H from a lateral point of access LP such that the point of insertion is substantially perpendicular to the sagittal plane S. Alternatively, the point of insertion can be posterior of the lateral point of access LP, for example up to about 45 degrees posterior to the lateral point of access LP. In some embodiments, the point of insertion can be anterior to a lateral point of access. For example, a surgeon can approach anterior to the Carotid artery and the Jugular vein and can retract a sheath used to insert the implant posterior following insertion.

After the incision is formed, and after any desired or necessary preparation of the space between the vertebrae, an implant can be inserted through the incision and to a desired implant location. Alternatively, an access port can be inserted into the incision to form an insertion channel and the implant can be inserted therethrough and placed at a desired implant location. In one exemplary embodiment the desired implant location is in the cervical region of the spine, preferably between any two of the vertebrae in the C3 through C7 region, and more particularly is configured to be disposed between the C4 and C5 vertebrae. The distal end of the cage member can first be inserted into the space between the desired vertebrae, and then the implant can be rotated to the desired implant location. In one exemplary embodiment the cage member can fill about one-third to about two-thirds of the footprint of a vertebral body.

As explained above, the implant is shaped to match the contours of the desired implant location. Accordingly, in one exemplary embodiment the superior and inferior surfaces 22, 22' and 24, 24' are configured to substantially match the anatomy of a central to posterior portion of adjacent vertebral bodies such that the implant 10, 10' can be rotated to and then implanted at a central to posterior portion of the adjacent vertebral bodies. This implant location can be desirable in order to successfully navigate the uncinate processes. In other embodiments the anterior wall 26, 26' of the cage member 20, 20' can be substantially aligned with the curve of the anterior portions of the vertebrae. In still other embodiments the implant 10, 10' can be implanted at an angle with respect to a spine. Thus, while the embodiment illustrated in FIG. 3A shows the implant 10' at zero degrees (i.e., aligned with the transverse axis of the subject's body), in other embodiments the implant can be placed at an angle with respect to the transverse axis at a range between about 1 degree and about 89 degrees, and more preferably between about 30 degrees and about 45 degrees. The angle can be created during the act of inserting the implant through the incision, or any time thereafter, including at the site of the vertebral bodies.

In embodiments that include a plate member, such as the implant 10, the plate member 50 can be positioned so that it is adjacent to the vertebrae, closer to the anterior portion of the spine. The plate member 50 can then be fixed to one or both of the vertebrae such that the midpoint M of the plate member 50 is disposed anterior to the long axis $L_1$ of the cage member 20. Bone graft or bone growth-promoting material can be incorporated into the cage member before, during, or after insertion is complete.

Intra-Facet Fusion Screws and Staples

Another spinal implant for use in treatment of the cervical region of the spine, referred to herein as an intra-facet fusion screw, is illustrated in FIGS. 6A-12B. Another implant, referred to herein as an intra-facet staple, is illustrated in FIGS. 13A and 13B. The screws and staples can be used by themselves as spinal implants, and are designed to be implanted directly between two facets between the diarthrodial surfaces of the facet joint.

Figure 6A:
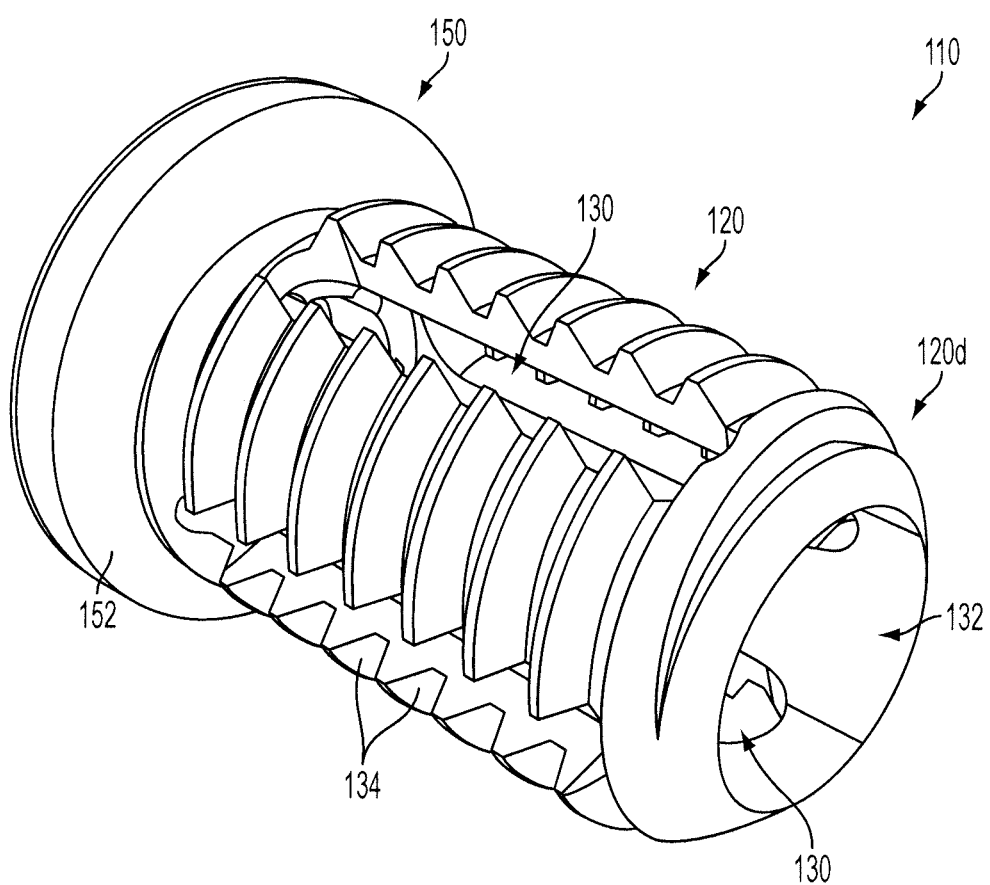
FIG. 6A is a distal perspective view of another exemplary embodiment of a spinal implant that is threaded and includes a tapered distal end.
Figure 6B:
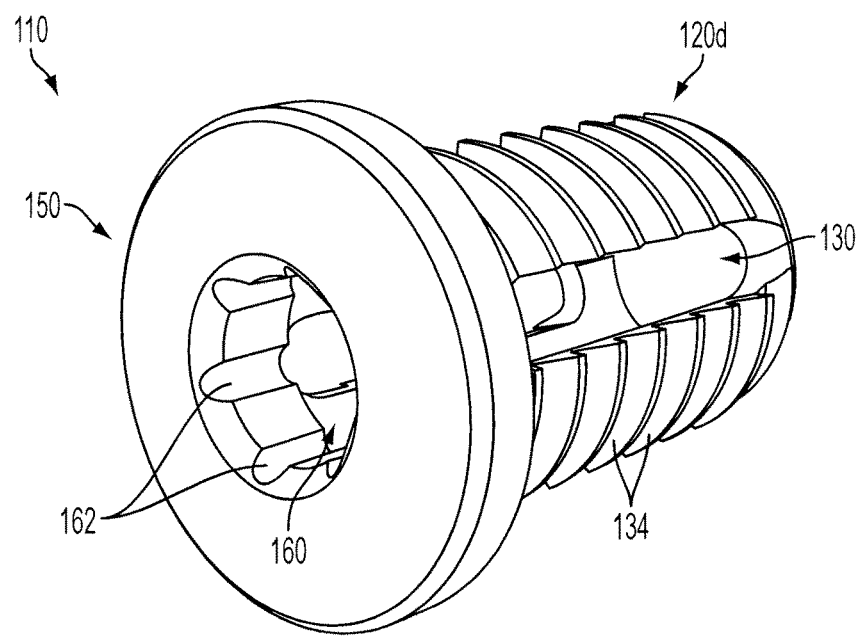
FIG. 6B is a proximal perspective view of the spinal implant of FIG. 4A.
Figure 6C:
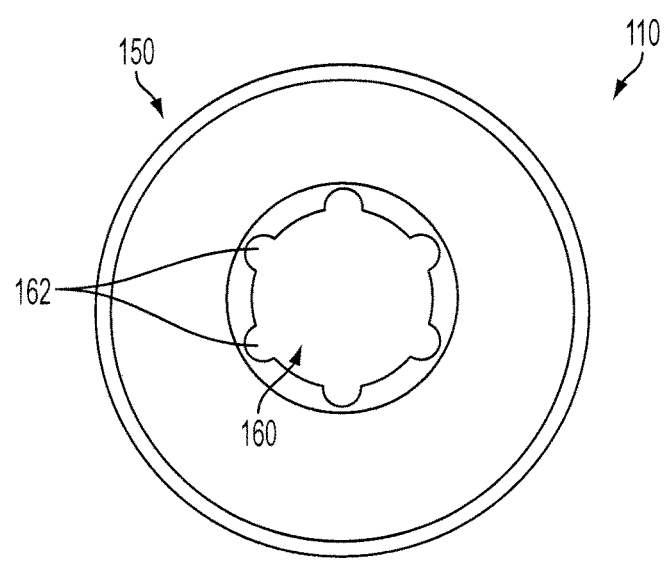
FIG. 6C is a proximal view of the spinal implant of FIG. 4A.

In one embodiment of an intra-facet screw 110, illustrated in FIGS. 6A-6C, the screw 110 can include a body portion 120 and a head portion 150. As illustrated, the body portion 120 can be generally cylindrical, hollow, and can include one or more relief slits or openings 130 in its surface to allow bone graft or bone growth-promoting materials to be disposed therein. In the illustrated embodiment there are four elongate openings 130, although the number, size, and shape of the openings can vary across different embodiments, as will be appreciated by a person skilled in the art. A bore 132 extending through the body portion 120 can be any shape, and the shape need not match the shape of the body portion 120. However, in the illustrated embodiment the bore 132 is generally cylindrical and extends from the head portion 150 all the way through a distal end 120d of the body portion 120.

The body portion 120 can have threads 134 formed on an external surface, allowing the screw 110 to be more easily placed between opposed superior and inferior surfaces of the facet joint. Further, the threads 134 can also provide additional grooves on which bone graft and bone growth-promoting materials can be disposed. In the illustrated embodiment the distal end 120d is tapered, which provides additional assistance in placing the screw 110 in a desired location. The body portion 120 can also be configured to be expandable, which can assist in positioning the screw 110 in a desired location and subsequently holding the screw 110 in place. While a person skilled in the art will recognize a number of features that can be incorporated into the screw 110 to make it expandable, in some embodiments the relief slits or openings 130 themselves can provide that capability. In other instances, an expandable material can be used as part of the structure of the screw 110.

A diameter of the head portion 150 can generally be greater than a diameter of the body portion 120. As a result, the screw 110 can be stopped at a desired location by abutting a distal surface 152 of the head portion 150 against bone near the desired location. A bore 160 of the head portion 150 that corresponds with the bore 132 of the body portion 120 can also include additional features to assist in mating with insertion instruments. As shown, a hex-screw head having a series of six grooves 162 is provided in the bore of the head portion to allow a similarly-shaped insertion instrument to engage the screw 110 for implantation. Although the head portion 150 is illustrated as being generally cylindrical or spherical, in some embodiments the head portion can be configured to have a shape that is complementary to a shape of the facet against which it is designed to rest.

One skilled in the art will appreciate that the implant can be made from any number of biologically-compatible materials used to form spinal implants, including materials that are partially or fully bioresorbable. Exemplary materials include titanium, titanium alloys, polyether ether ketone (PEEK), reinforced PEEK, and Nitinol®. Further, in some embodiments different portions of the screw may be made of different materials. For example, the head portion may be made from a different material than the body portion or a distal end of the body portion may be made from a different, possibly harder material, than the remainder of the body portion.

While the screws can have a number of shapes and sizes, in some embodiments a diameter of the body portion 120 is approximately in the range of about 5 millimeters to about 19 millimeters while a diameter of the head portion 150 is approximately in the range of about 7 millimeters to about 22 millimeters. The size of the diameter of the body portion 120 and the size of the diameter of the head portion 150 can depend on each other, and in one embodiment the diameter of the body portion is approximately in the range of about 5 millimeters to about 6 millimeters and the diameter of the head portion is approximately in the range of about 7 millimeters to about 8 millimeters. Further, in some embodiments, a length of the body portion 120 can be approximately in the range of about 7 millimeters to about 30 millimeters. In one embodiment the length of the body portion 120 is approximately in the range of about 10 millimeters to about 12 millimeters. Other shapes and designs can be used depending on the location that the screws 110 are intended to be implanted. Still further, while the illustrated embodiment shows the screw 110 as a unitary component, in other embodiments the body portion 120 can be disengaged from the head portion 150 or the body portion 120 can be broken apart into two or more sections.

Figure 7:
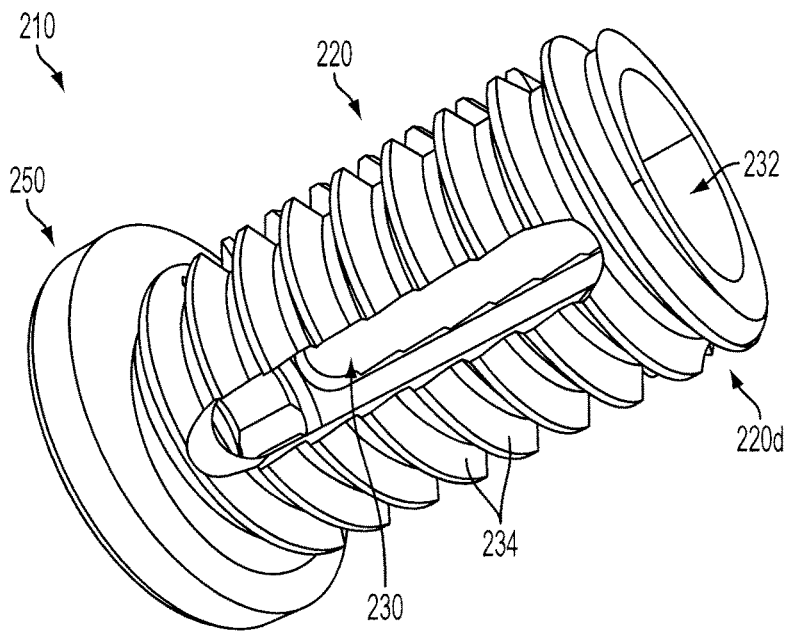
FIG. 7 is a distal perspective view of an exemplary embodiment of a spinal implant that is threaded and has a non-tapered distal end.

A number of other embodiments of facet screws 210, 310, 410, and 510 are also provided in FIGS. 7-10. The screw 210 of FIG. 7 includes a body portion 220 having a plurality of threads 234 disposed thereon, a bore 232 extending therethrough, and a plurality of elongate relief slits or openings 230 formed therein. A head portion 250 is integrally formed with the body portion 220. The screw 210 of FIG. 7 differs from the screw 110 of FIGS. 6A-6C because a distal end 220d of the body portion 210 of FIG. 7 is not tapered.

Figure 8:
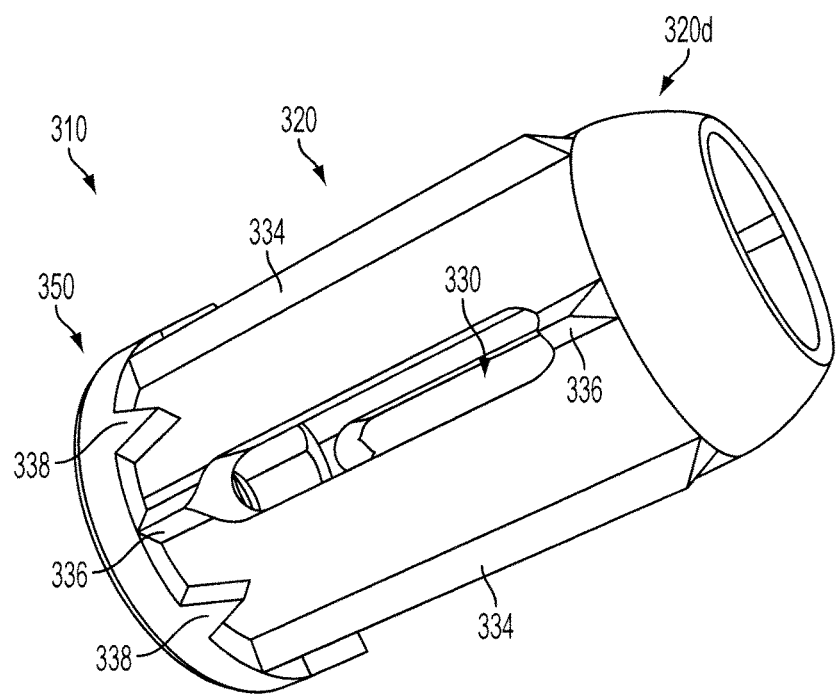
FIG. 8 is a perspective view of another exemplary embodiment of a spinal implant that includes a plurality of edges and spikes disposed around a circumference thereof.

FIG. 8 illustrates another embodiment of an intra-facet screw 310. The screw 310 includes a body portion 320 having a bore 332 extending therethrough and a head portion 350. A diameter of the head portion 350 can be larger than a diameter of the body portion 320. However, as illustrated, the difference between the diameters of the body and head portions 320 and 350 in the screw 310 is not as pronounced as in embodiments shown in FIGS. 6A-6C and 7. Further, unlike the embodiments of FIGS. 6A-6C and 7, the body portion 320 is not threaded. Instead, a plurality of edges 334, 336 is formed on the body portion 320. Some of the edges 334 extend along most of the length of the body portion 320, while other edges 336 are formed on either end of elongate openings 330 in the body portion 320. Like the other embodiments, any number of relief slits or openings 330 can be formed in the body portion 320.

As illustrated, a distal end 320d of the body portion 320 is tapered, and although in the illustrated embodiment the edges 334, 336 do not extend onto the tapered distal end 320d, in other embodiments the edges 334, 336 can extend onto the tapered distal end 320d. Further, a plurality of spikes 338 can be formed around a circumference of the screw 310 such that the spikes 338 extend from the head portion 350 and onto the body portion 320. The spikes 338 can assist in maintaining a location of the screw 310 as it is implanted in a desired location.

Figure 9:
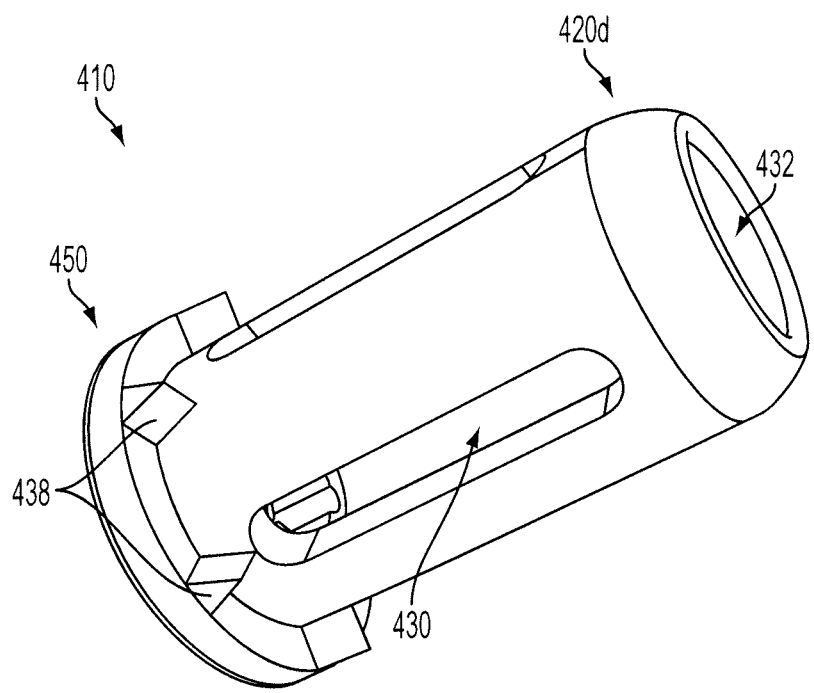
FIG. 9 is a perspective view of yet another exemplary embodiment of a spinal implant that includes a plurality of spikes disposed around a circumference thereof.

Yet another embodiment of an intra-facet screw 410 is illustrated in FIG. 9. The screw 410 of FIG. 9, which is similar to the screw in FIG. 7, includes a body portion 420 having a bore 432 extending therethrough, a plurality of elongate relief slits or openings 430 formed in the body portion 420, a tapered distal end 420d, and is not threaded. Further, a head portion 450 includes a plurality of spikes 438 around a circumference of the screw 410 and that extend onto the body portion 420.

Figure 10:
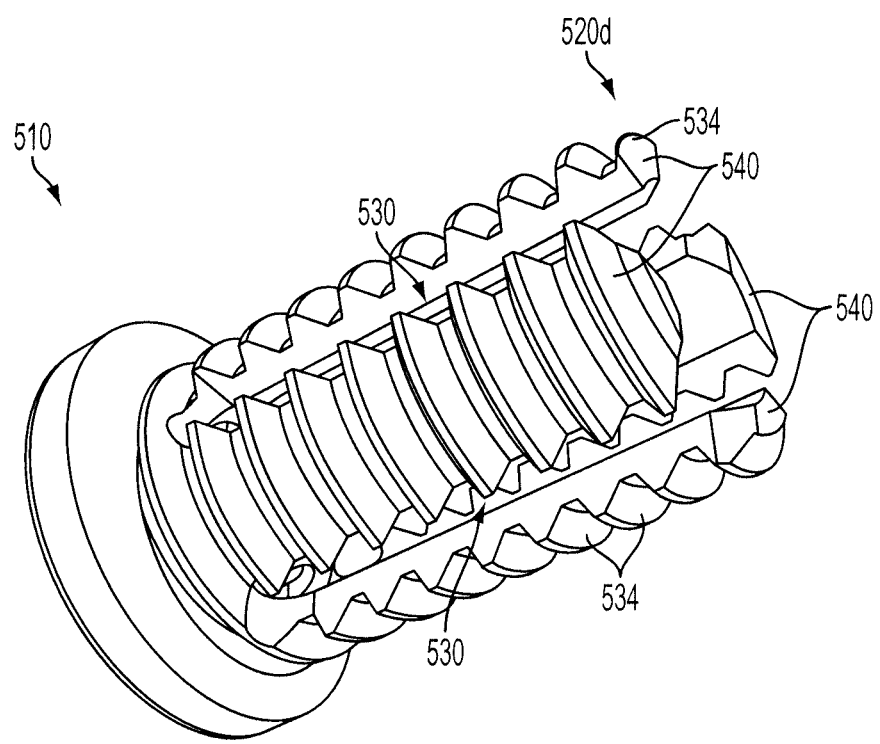
FIG. 10 is a perspective view of still another exemplary embodiment of a spinal implant that is threaded and includes a plurality of fingers.

Still a further embodiment of an intra-facet screw 510 is illustrated in FIG. 10. The screw 510 of FIG. 10 is more closely akin to the screws 110 and 210 of FIGS. 6A-6C and 7 because the screw 510 includes a body portion 520 having a bore 532 extending therethrough and threads 534 formed thereon, as well as a head portion 550 that has a diameter that is significantly larger than a diameter of the body portion 520. While the body portion 520 does include a plurality of relief slits or elongate openings 530 formed therein, the openings 530 do not close at the distal end 520d. This results in the formation of an elongate body that includes four fingers 540. This embodiment can provide additional flexibility in implanting the screw 510 in a desired location because the distal end 520d can be easier to manipulate in and out.

Figure 11A:
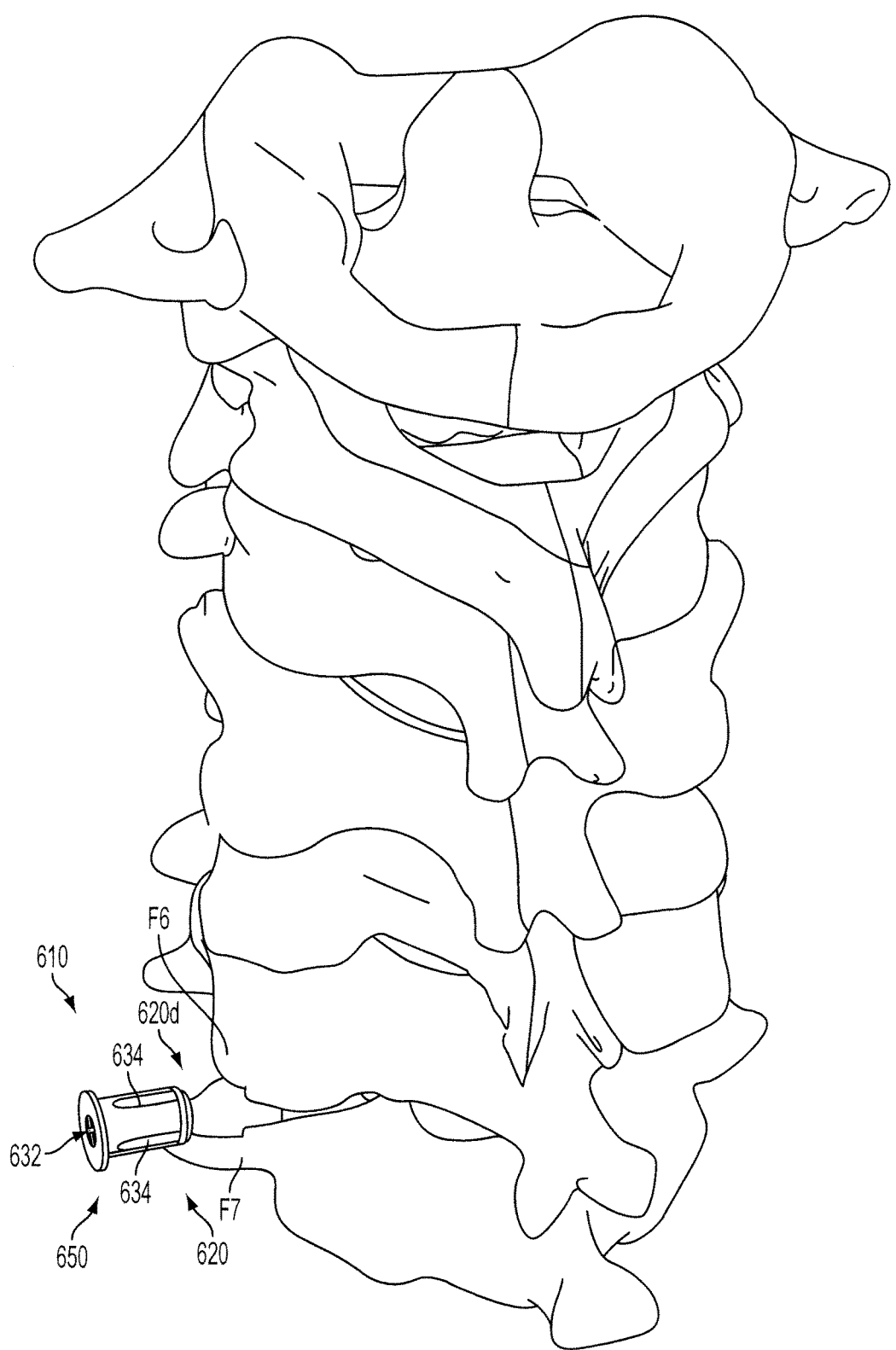
FIG. 11A is a schematic view of an exemplary embodiment of a spinal implant that includes a plurality of edges disposed around a circumference thereof before it is disposed between two vertebrae.
Figure 11B:
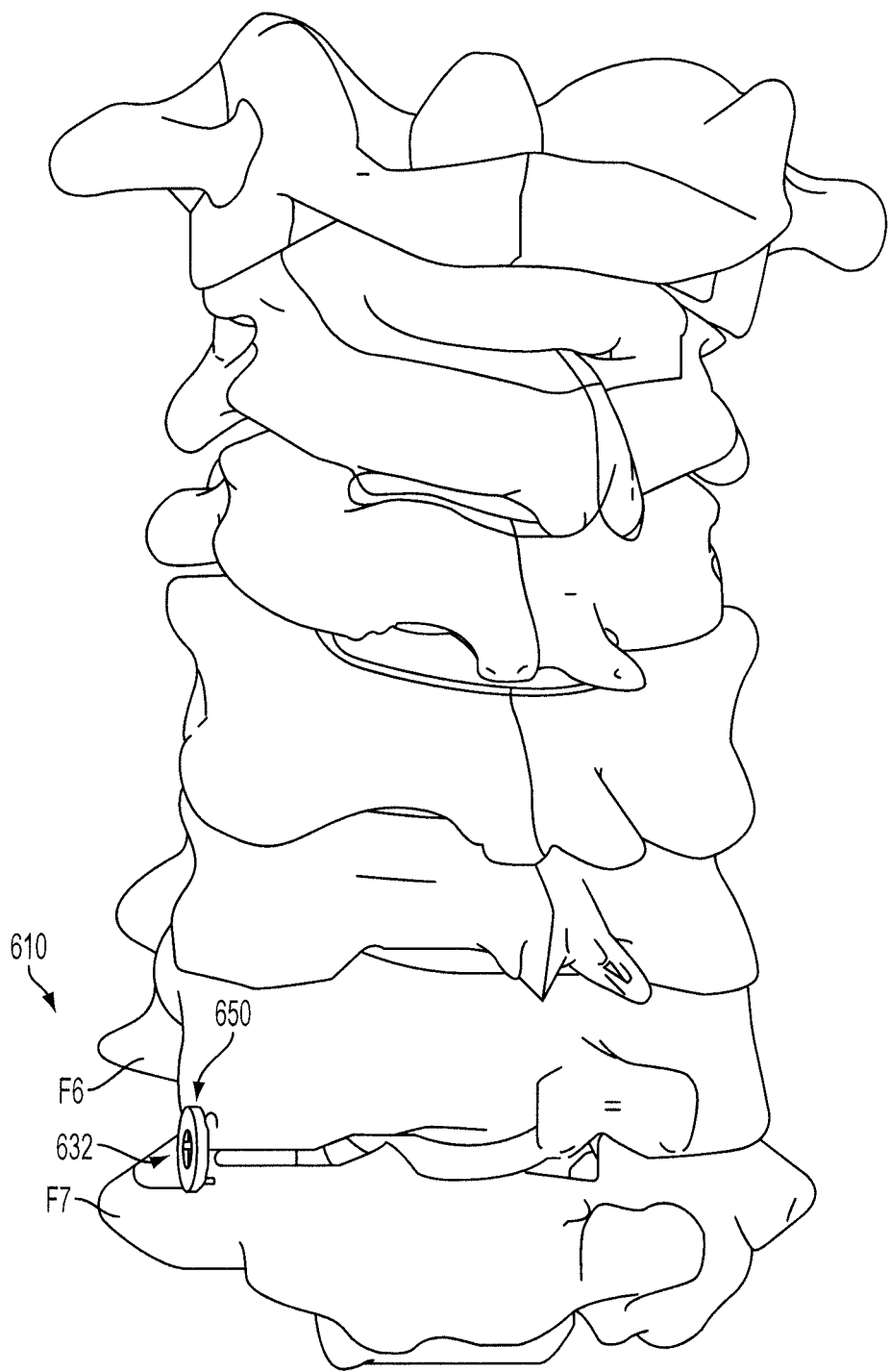
FIG. 11B is a schematic view of the spinal implant of FIG. 9A after it is disposed between two vertebrae.

One method of using implants of the nature illustrated and described with respect to FIGS. 6A-10 is illustrated by FIGS. 11A and 11B. As shown, an intra-facet screw 610 having a body portion 620 and a head portion 650 can be disposed adjacent of a desired implant location in the cervical region of the spine. The screw 610 can be placed at a desired location in a manner similar to the methods described above for implanting the implants of FIGS. 2A-3. Thus, for example, a lateral or posterior-lateral incision can be formed in an area near the cervical region of the spine and the intra-facet screw 610 can be inserted through to the cervical region of the spine directly, or through a port placed in the incision. An angle of insertion can be substantially perpendicular to the sagittal plane of a subject, or it can be at an angle posterior to perpendicular to the sagittal plane, as shown for example in FIG. 1.

After the intra-facet screw 610 is in the vicinity of its desired implantation site, it can be pushed between two adjacent facet joints, as shown facet joints F6 and F7, until a distal surface of the head portion 650 of the screw 610 is flush against a portion of the bone. In other embodiments the screw can be inserted even further such that a proximal surface of the screw is flush with the bone or passes beyond the surface of the bone. Bone graft or bone growth-promoting material can be added to the screw 610 after insertion is complete, for instance through a bore 632. In embodiments in which the body portion 620 is threaded or in which there are openings formed in the body portion 620, the bone graft or bone growth-promoting material can be associated with those portions before, during, or after implantation.

Figure 12A:
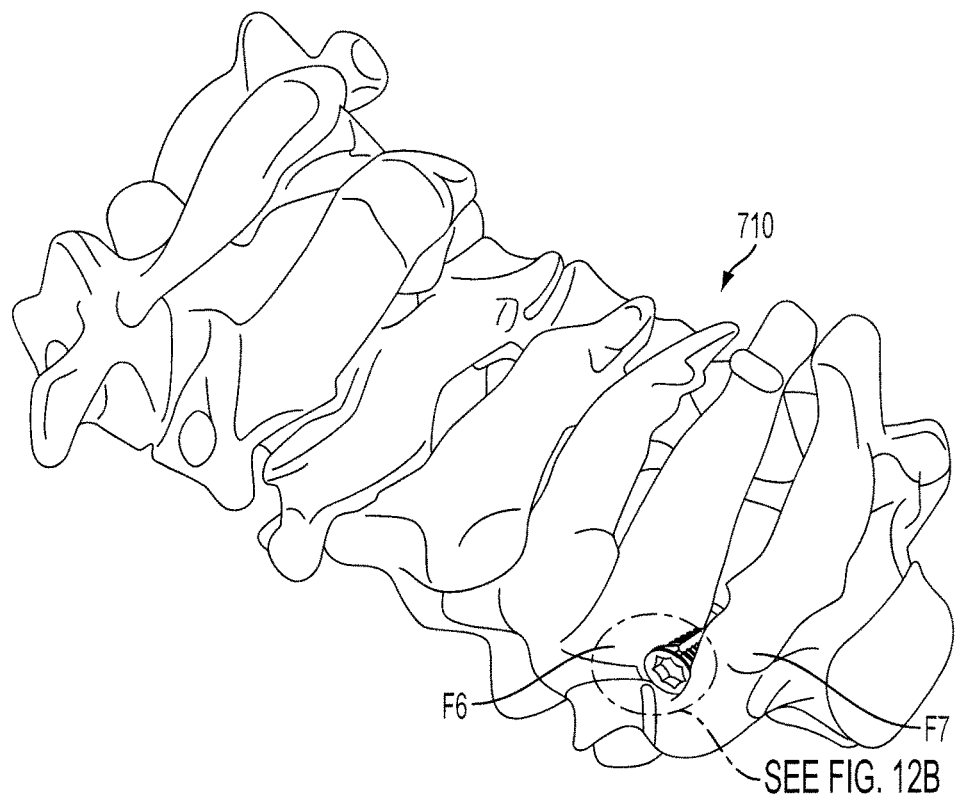
FIG. 12A is a schematic view of another embodiment of a spinal implant that is threaded and is disposed between two vertebrae.
Figure 12B:
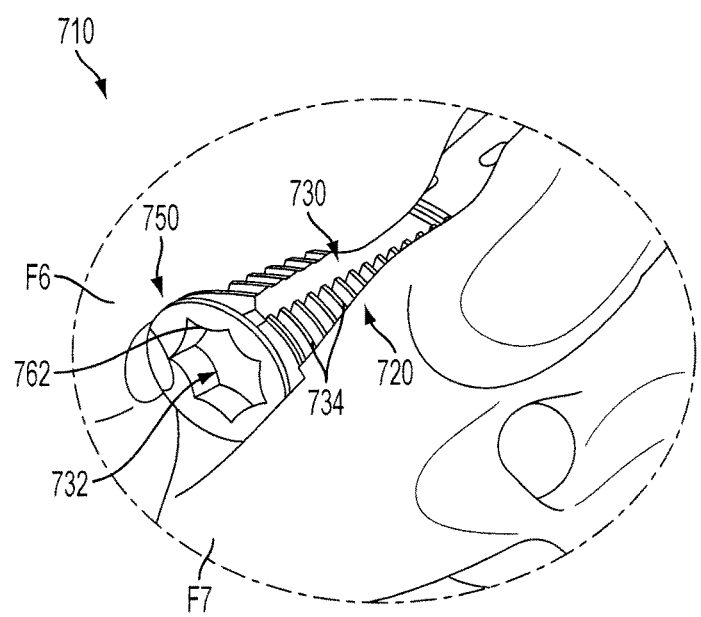
FIG. 12B is a detail view of the spinal implant of FIG. 10A.
Figure 13A:
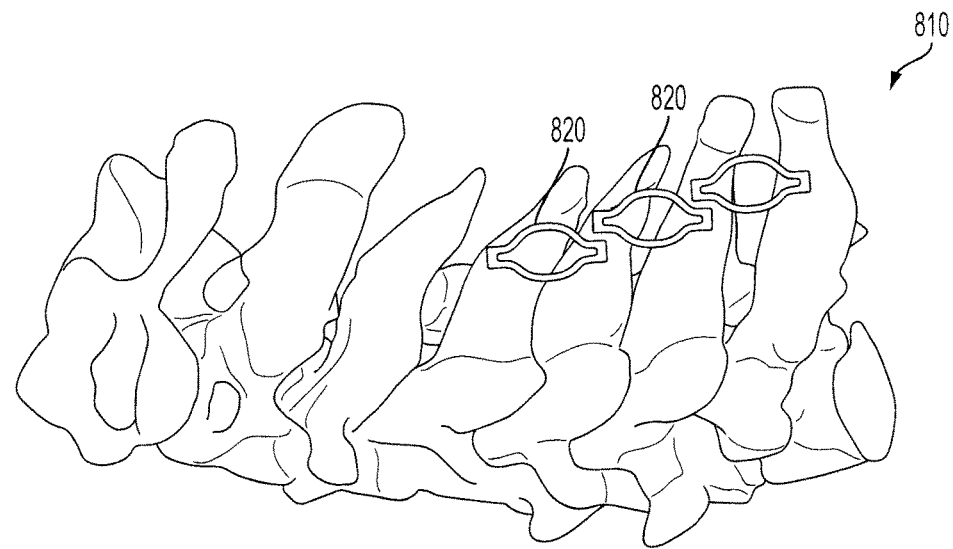
FIG. 13A is a perspective view of an exemplary embodiment of a spinal implant that includes lateral staples and is attached to a cervical region of a spine.
Figure 13B:
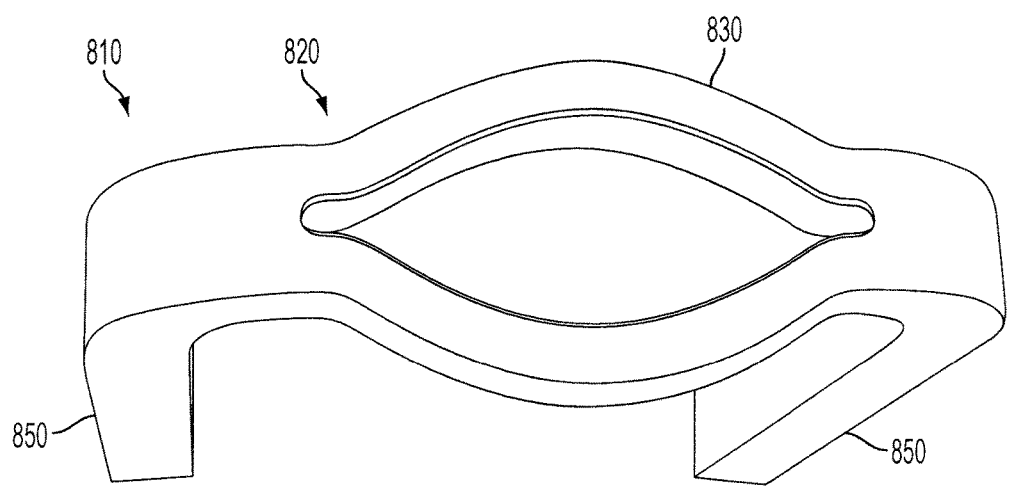
FIG. 13B is a perspective view of a lateral staple for use implantation in a cervical region of a spine.

FIGS. 12A and 12B illustrate another intra-facet screw 710 disposed in a cervical region of the spine. Implantation of this screw 710 can be performed in a manner similar to the manner described with respect to FIGS. 11A and 11B. As shown, threads 734 of a body portion 720 can engage the adjacent facet joints, as shown facet joints F6 and F7, when the screw 710 is driven into the space between the F6 and F7 facet joints and the screw 710 comes to rest when a head portion 750 engages the bone. The screw 710 includes a hex-head 762 such that a hex-shaped insertion instrument can be used to drive the screw 710 into its desired location. After the insertion instrument is removed, any areas not already filled with bone graft or bone growth-promoting material can be filled with such a material, including a bore 732 extending through the body portion 720, openings 730 in the body portion, and the threads 734.

FIGS. 13A and 13B illustrate another embodiment of a spinal implant 810. The implant 810 includes lateral staples 820 configured to be disposed between lamina of the spine, or adjacent structures such as the spinous process. As shown in FIG. 13B, the staples can include an elliptically-shaped central portion 830 and engaging arms 850. The staples 820 can be made of a temperature-sensitive material, such as Nitinol®, such that the staples can assume a desired configuration upon delivery between adjacent vertebrae. As a temperature increases, the central portion 830 can expand and the engaging arms 850 can close. In one embodiment the staple 820 is delivered so that the engaging arms 850 are disposed partially in adjacent lamina. As the temperature increases, the central portion 830 expands and the engaging arms move toward each other, causing the adjacent lamina to be pulled together.

Other shapes of staples can be used. Additionally, the dimensions of such staples can vary, depending on spacing between lamina that exists and the desired spacing between lamina. For example, a length of a staple from one arm to the other arm can be about 10 millimeters to about 50 millimeters. In one embodiment it can be about 12 millimeters and in another embodiment it can be about 20 millimeters. Likewise, a length of an arm itself can vary, and can be in the range of about 6 millimeters to about 20 millimeters. In one embodiment a length of one arm can be about 6 millimeters and a length of another arm can be about 10 millimeters. In some embodiments the staples can be asymmetric such that the length of one arm is different than the length of the second arm of the same staple, while in other embodiments the lengths of each arm can be substantially equal. Further details about staples that can be adapted for use as a spinal implant in view of the teachings contained herein are found in U.S. Pat. No. 5,779,707, the contents of which is incorporated by reference in its entirety.

A number of methods can be used to implant staples of the nature described with respect to FIGS. 13A and 13B. For example, in embodiments in which the staples are temperature-controlled, the staples can first be brought to a temperature at which its arms are open for implantation. In one exemplary embodiment, the staples are kept for at least two hours at a maximum temperature of about 0° F. (−18° C.). Following the formation of an incision to implant the staples, using techniques described herein for instance, the implantation site can be prepared to receive the staples. This can include using any number of guides, drills, and wires, among other instruments, to prepare vertebral bodies for receiving the staples. For example, temporary pins can be used to prevent displacement of structures at or adjacent to the implantation site. Likewise, guides can be used to place the vertebral bodies at an ideal location for receiving the staples.

Once the implantation site is properly prepared, one of the staples can be inserted to the surgical location and implanted such that a first arm of the staple is driven into a portion of a first vertebral body and a second arm of the staple is driven into a portion of a second vertebral body. A surgical stapler, impactor, such as a Memory arthrodesis impactor, or any other known tool for applying staples, can be used to implant the staples. Further, any number of instruments can be used to assist with the insertion of the staples, such as guides and pins.

Once the staple is located in its desired location, any instruments used to assist with the preparation of the implantation site or the implantation of the staple can be removed. Further, the arms can be actuated toward a central portion of the staple to close the arms. This can result naturally from the temperature of the surgical location, which is higher than the starting temperature of the staples, or a surgeon can control the temperature at the surgical site to assist in the actuation of the arms. Actuation of the arms results in the vertebral bodies in which the arms are engaged being drawn toward each other. Other staples can be implanted in a similar manner.

Although in the embodiment illustrated in FIG. 13A the staples 810 are implanted in adjacent vertebral bodies, in other embodiments the staples can span across two or more vertebral bodies. Further, additional methods for operating staples of the nature disclosed herein can be found in the Memory Staple Surgical Technique, a publication distributed by DePuy Spine, Inc., a Johnson & Johnson company, the contents of which is incorporated by reference in its entirety. Although the techniques described in that publication are generally directed to implantation in a subject's foot, a person skilled in the art would be able to adapt those techniques for use in vertebral bodies based on the disclosures contained herein.

Lateral Posterior Fusion

Other implants for use in a cervical region of the spine can include one or more spinal fixation elements, such as rod members, capable of extending across a plurality of vertebral bodies. A person skilled in the art will recognize that the use of spinal stabilization members in the cervical region of the spine can be helpful in treating a variety of abnormalities. The spinal stabilization members of the present invention, which are illustrated in FIGS. 14A-21B, are particularly useful because they provide the mobility and flexibility of using a rod while also providing the benefit of having multiple fixation points. Spinal fixation elements disclosed herein avoid some of the drawbacks associated with previously known spinal fixation elements, which have limited placement flexibility due to the need to affix them to the spine with separate plate members or other attachment means. The use of fixation points that are formed on the rod itself dramatically increases the number of points at which the rod members can be fixed. By increasing the number of fixation points at which the rod member can be fixed, the spinal fixation elements become substantially more versatile for use in the cervical region of the spine. The number of possible implant locations increases, and thus, the number of possible rod designs increases.

Figure 14A:
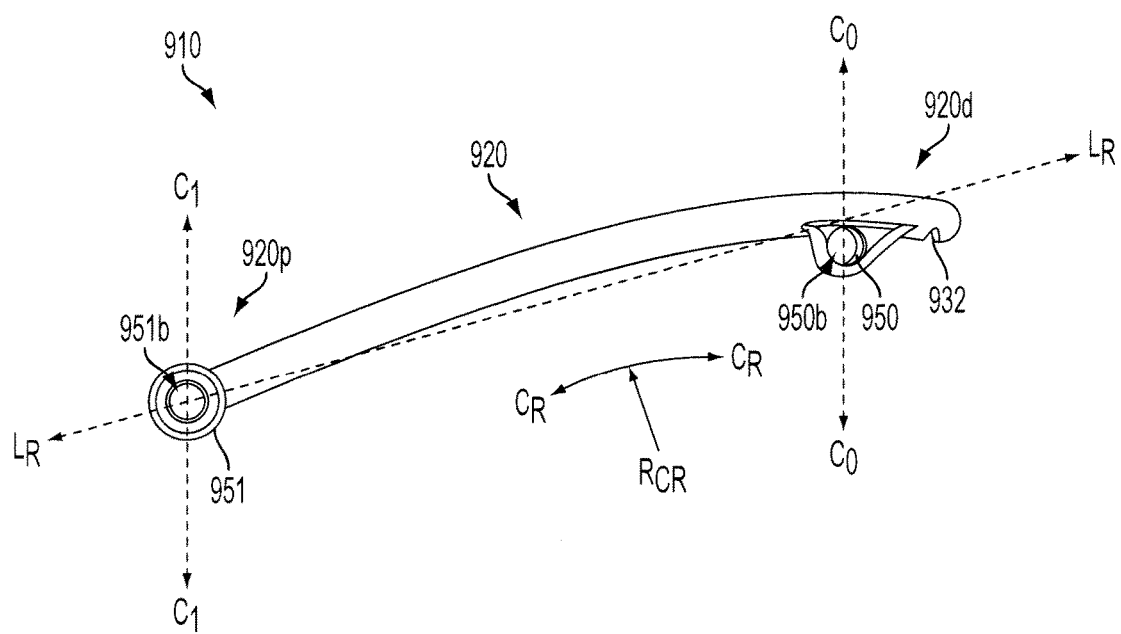
FIG. 14A is a perspective view of one exemplary embodiment of a spinal implant that includes a rod member having mounting eyelets.
Figure 14B:
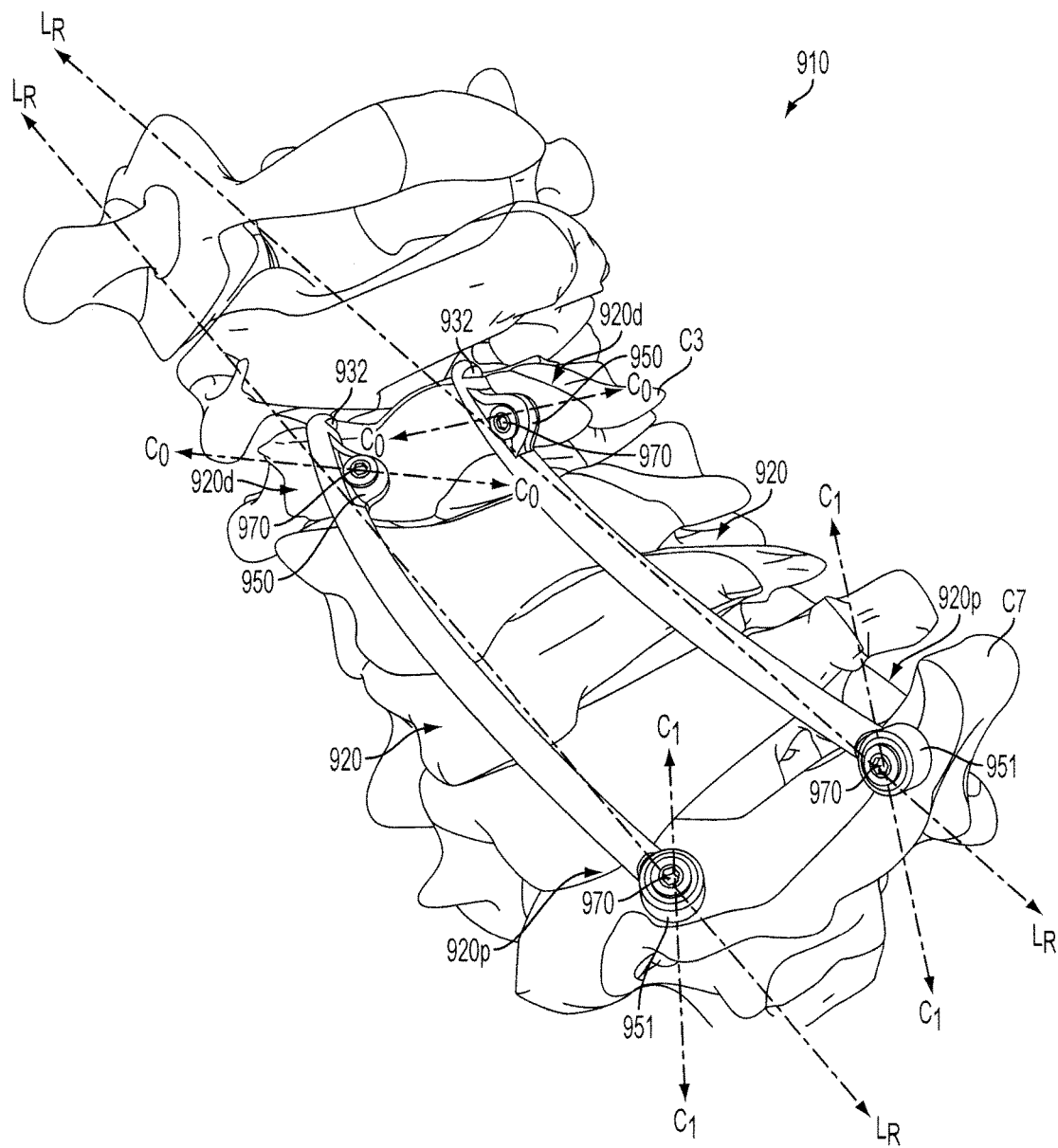
FIG. 14B is a perspective view of the two spinal implants of FIG. 12A attached to a cervical region of a spine.

One exemplary embodiment of a spinal implant 910 that includes a rod member 920 for use in treating the cervical region of the spine is illustrated in FIGS. 14A and 14B. FIG. 14A illustrates a single, elongate rod member 920, while FIG. 14B illustrates two rod members 920 implanted in a cervical region of a spine. Anchor members 970, such as bone screws, can be used to secure the rod members 920 at desired locations in one or more of the vertebrae.

In the exemplary embodiment illustrated in FIG. 14A, the rod member 920 is generally elongate between its proximal and distal ends 920p, 920d. While the rod member 920 can be substantially straight, in the illustrated embodiment the rod member 920 is curved at least in one plane. Those skilled in the art will appreciate that the curve of the rod member can take any shape needed to address a patient's condition. In instances in which a patient suffers from lordosis or another condition, a curve can be substantially similar to a curve of the spine that results from lordosis or another condition. In some embodiments, a plurality of shorter rod members can be used to allow for a profile of a spine to be biomechanically matched. Alternatively, a longer rod member can be designed to biomechanically match a spine profile. A radius $R_R$ of a curve $C_R$ of the rod member 920 can be in the range of about 0 millimeters to about 500 millimeters, and in one embodiment the radius $R_R$ is about 4 millimeters. A person skilled in the art will recognize that the radius of the curve of a spinal fixation element may change throughout its distribution because the curve can be asymmetric.

In embodiments in which the rod member 920 includes a curve, the curve can be pre-determined. Alternatively, the rod member 920 can include some flexibility or malleability to allow it to be shaped as desired by a surgeon at the time of a surgical procedure. In other instances the rod member 920 can be fully bendable so it can be formed into any desired shapes across its length. In one embodiment the rod member 920 is substantially S-shaped, while in another embodiment it is substantially Z-shaped. Any number of shapes can be achieved by the rod member 920. Likewise, the rod member 920 can have any size. It can be sized for use in the cervical region of the spine, and more particularly to extend between any length between the C1 and C7 vertebrae. As shown in FIG. 14B, the rod member 920 extends between the C3 and the C7 vertebrae. The length of the rod member can be in the range of about 20 millimeters to about 250 millimeters, and in one embodiment can be about 35 millimeters Likewise, the rod member can have a variety of thicknesses. For example, the rod member can have a thickness in the range of about 3 millimeters to about 20 millimeters, or in the range of about 3 millimeters to about 5.5 millimeters, and in one embodiment can be about 4 millimeters. The rod member can also have a variety of cross sectional shapes, including circular, ovoid, square, rectangular, triangular, etc.

The rod member 920 can include features configured to assist with its implantation at a desired surgical location. In the illustrated embodiment the distal end 920*d* includes a V-shaped notch 932, which is complementary to a distal end of an insertion instrument such that the insertion instrument can engage the rod member 920 at the V-shaped notch 932 to direct the rod member 920 to a desired location. Although in the illustrated embodiment the notch 932 is V-shaped, any number of shapes and configurations can be used to assist in mating an insertion instrument with the rod member 920. Likewise, a person skilled in the art will recognize other ways by which the notch 932 can be used to insert the rod member 920 to a desired surgical location.

The rod member 920 can also include one or more mounting eyelets 950, 951. As shown, the rod member 920 includes two mounting eyelets—the first mounting eyelet 950 is disposed in proximity to the distal end 920*d* and the second mounting eyelet 951 is at the proximal end 920*p*. The eyelets 950, 951 can be located anywhere along a length of the rod member 920. Thus, in some embodiments an eyelet can be located at each of the proximal and distal ends 920*p*, 920*d*, while in other embodiments an eyelet can be located in proximity to a distal end 920*d* and a second eyelet can be located in proximity to a proximal end 920*p*, but neither being at a terminal end of the rod member 920. Eyelets can even be located centrally along a length of the rod member 920. In some embodiments, eyelets can be slidably coupled to the rod member such that the location of the eyelets can be moved to desired locations at a surgical site.

The mounting eyelets 950, 951 can either be in-line with a longitudinal axis $L_R$ of the rod member 920 or offset from the longitudinal axis $L_R$. For example, FIGS. 14A and 14B illustrate that the second mounting eyelet 951 is approximately in-line with the longitudinal axis $L_R$, while the first mounting eyelet 950 is offset from the longitudinal axis $L_R$. More particularly, a central axis $C_1$ of the second mounting eyelet 951 intersects the longitudinal axis $L_R$ while a central axis $C_O$ of the first mounting eyelet 950 is offset from the longitudinal axis $L_R$. Either or both of the eyelets 950, 951 can be selectively located approximately in-line with the longitudinal axis $L_R$ or offset from the longitudinal axis $L_R$.

Likewise, any number of eyelets can be used in conjunction with the elongate rod member 920 in any number of configurations with respect to the eyelets being approximately in-line or offset from the longitudinal axis of the rod member. In instances in which the rod member includes a desired shape, such as an S-shape or a Z-shape, each eyelet can serve as a vertex of the desired shape. Thus, if a rod member 920' is substantially S-shaped, as illustrated in FIG. 15, a first and third mounting eyelet 950', 953' can be disposed on one side of a central axis CA' that bisects the rod member 920' and a second and fourth mounting eyelet 951', 955' can be disposed on the other side of the central axis CA'.

As shown, the first and second mounting eyelets 950', 951' are offset with respect to the rod member 920', while the third and fourth mounting eyelets 953', 955' are substantially in-line with respect to the rod member 920'. Further, the first and second mounting eyelets 950', 951' are in proximity to distal and proximal ends 920*d*', 920*p*', respectively, while the third and fourth mounting eyelets 953', 955' are disposed approximately at vertices A and B, respectively. As is the case with all of the embodiments in the present disclosure, other combinations of locations of eyelets can also be used with the rod member 920'.

The eyelets 950, 951 can be configured to receive a variety of anchoring members (e.g., hooks, bolts, wires, screws, anchors, etc.), but as shown the eyelets 950, 951 each include a circular bore 950*b*, 951*b* so that anchoring members 970, such as screws, can be disposed therethrough. In one embodiment the mounting eyelets 950, 951 can be configured such that anchoring members disposed therein need not be oriented to extend parallel to each other. That is, the eyelets can be designed to allow for polyaxial movement of the anchor members engaged therein. By way of example, an internal surface of the eyelets can be substantially spherical so as to correspond with a spherical head (not shown) of the anchor element such that the head can rotate relative to the eyelet as in a ball-in-socket joint.

Figure 15:
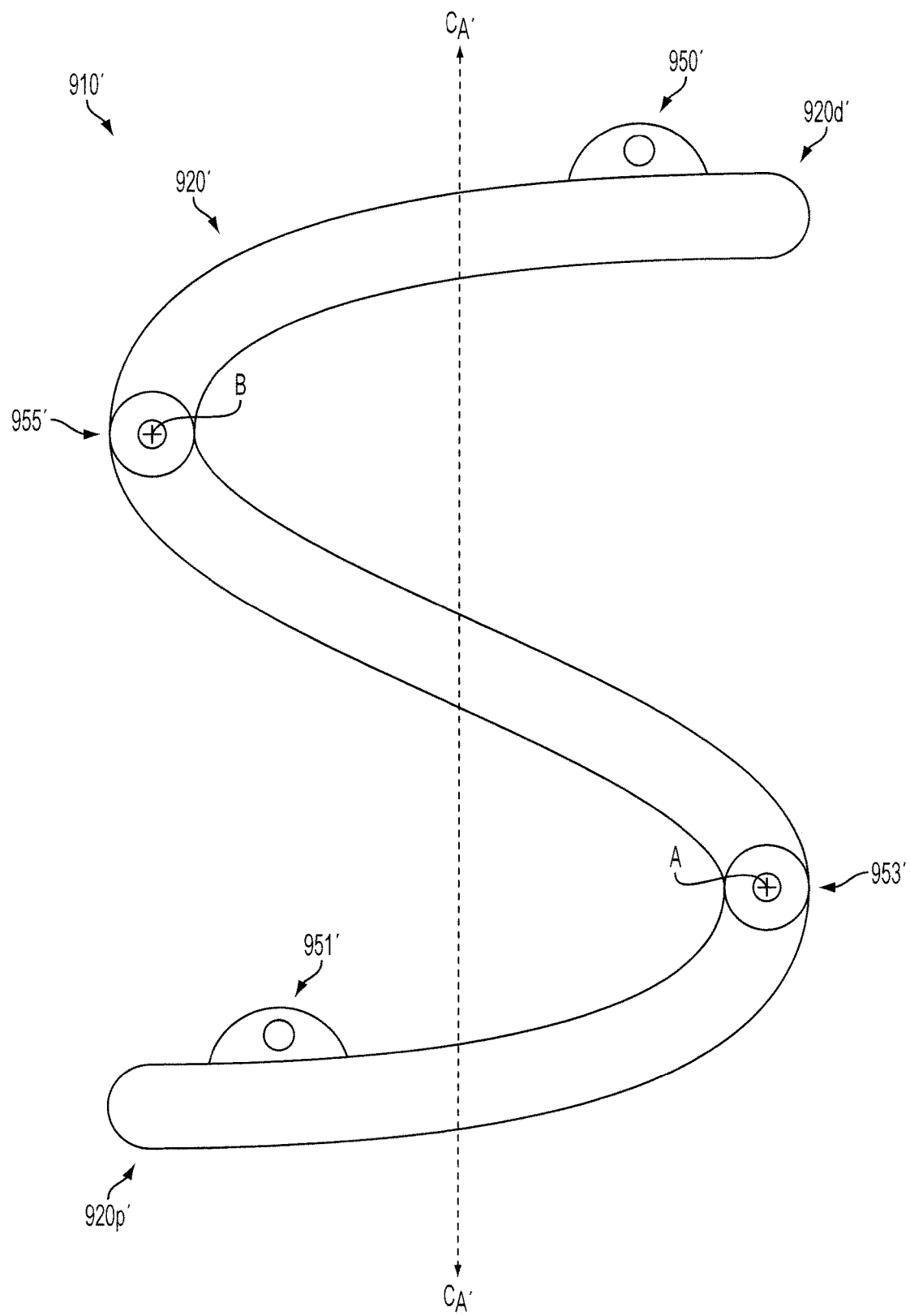
FIG. 15 is a schematic view of another exemplary embodiment of a spinal implant having a substantially S-shape.

Alternative spinal fixation elements are illustrated in FIGS. 15-21B. FIG. 15, as previously discussed, illustrates a rod member 920' having an S-shape having at least one vertex and having eyelets 950', 951', 953', and 955' disposed on either side of the central axis CA' that bisects the implant 910'.

Figure 16A:
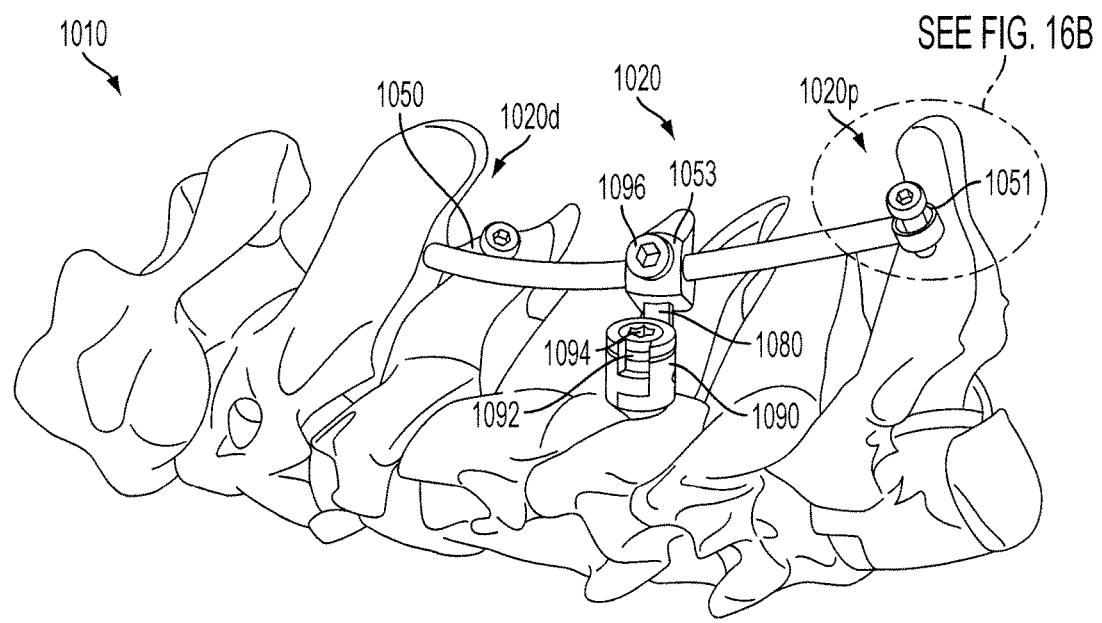
FIG. 16A is a perspective view of another exemplary embodiment of a spinal implant having a rod member coupled to a fixation element by way of a connector.
Figure 16B:
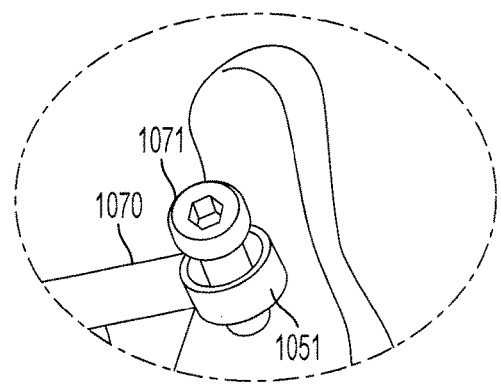
FIG. 16B is a detail view of a mounting eyelet of the spinal implant of FIG. 13A.

FIGS. 16A and 16B illustrate an embodiment of a spinal fixation element 1010 in which a rod member 1020 is used in conjunction with a connector 1080 and an anchor member 1090. As shown, the rod member 1020 includes an offset mounting eyelet 1050 in proximity to a distal end 1020*d* of the rod member 1020, an in-line mounting eyelet 1051 at a proximal end 1020*p* of the rod member 1020, and a third mounting eyelet 1053 disposed between the eyelets 1050 and 1051. As shown, the third eyelet 1053 is an in-line mounting eyelet that is slidably mounted upon the rod member 1020. Further, the third eyelet 1053 is configured to couple to the anchor member 1090 that is disposed adjacent to and offset from the rod member 1020 by way of the connector 1080, enabling the rod member 1020 to be secured to the spine at a location intermediate the eyelets 1050, 1051. This can be useful, for example, when part of a vertebra has been removed or lacks sufficient strength to receive an anchor member.

As shown in FIG. 16A, the connector 1080 extends between a connector housing 1092 of the anchor member 1090 and the eyelet 1053. The connector 1080 can be secured within the housing 1092 by a set screw 1094 and is secured to the third eyelet 1053 and the rod member 1020 by a set screw 1096. In use, the anchor member 1090 can secure the connector housing 1092 to a sound portion of the vertebra and, when properly positioned, the eyelet 1053 can be secured in its desired location using the set screw 1096. A person skilled in the art will recognize a variety of ways in which the slidable third eyelet 1053 can be secured to a vertebra offset from the rod member 1020 by way of the connector 1080 and anchor member 1090.

As more clearly shown in FIG. 16B, in some embodiments one or more of the mounting eyelets 1051 can include a pivoting or swivel feature. Such a feature provides additional flexibility in achieving a desired location for the rod member 1020. A screw 1070 can be selectively loosened to allow the rod member 1020 to move or swing to a desired location, and then the screw 1070 can be selectively tightened to engage the rod member 1020 and fix its location. Pivoting or swivel features of this nature can be incorporated to any of the mounting eyelets disclosed herein, and at any location across a length of the rod members.

Figure 17A:
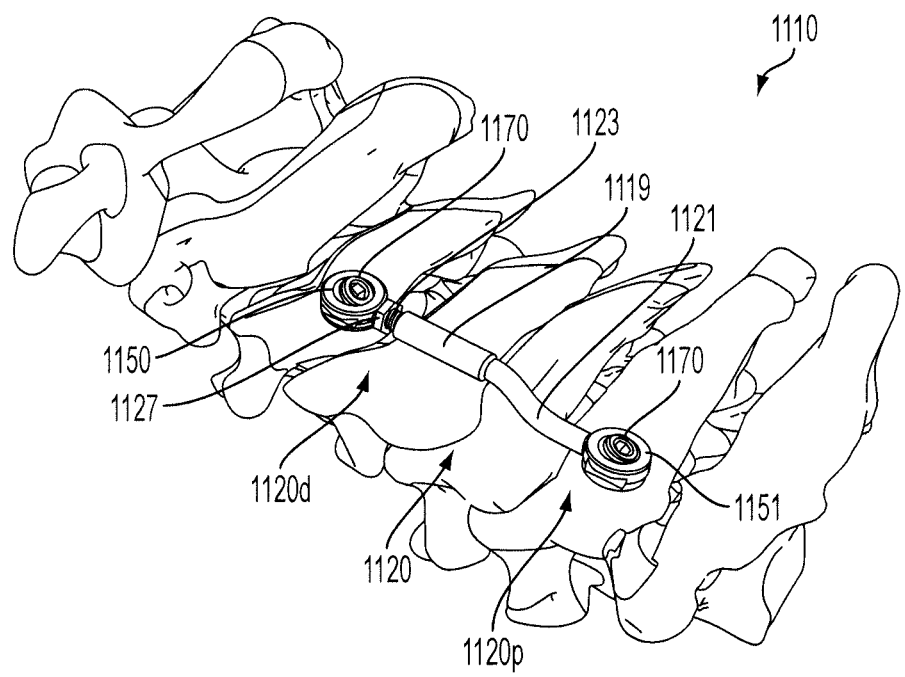
FIG. 17A is a perspective view of still another exemplary embodiment of a spinal implant having a telescoping rod member and that is attached to a cervical region of a spine.
Figure 17B:
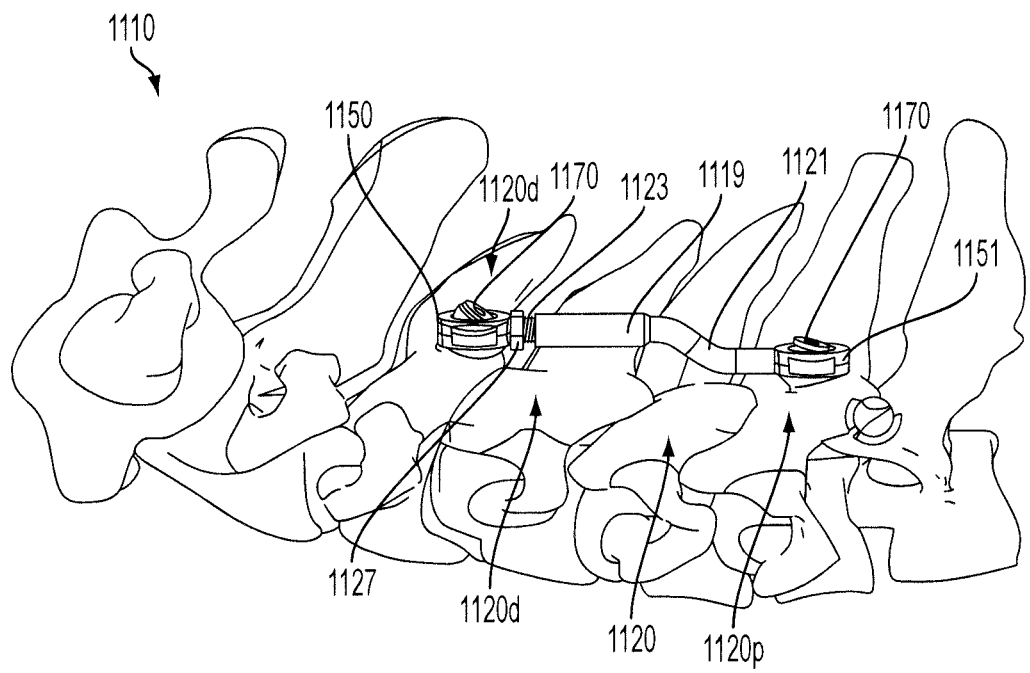
FIG. 17B is a perspective view of the spinal implant of FIG. 15A.

FIGS. 17A and 17B illustrate an implant 1110 in the form of a spinal fixation element having a telescoping feature, thereby allowing a length of a rod member 1120 to be selectively adjusted. As illustrated, a first segment 1119 of the rod member 1120 can have a bore with an internal diameter that is larger than an outer diameter of a second segment 1121. As a result, the first segment 1119 can receive the second segment 1121, enabling the first and second segments 1119, 1121 to slide with respect to each other such that the length between first and second mounting eyelets 1150, 1151, and thus the distance between distal and proximal ends 1120*d*, 1120*p* of the rod member 1120, can be adjusted. While any number of mechanisms can be used to adjust and subsequently fix the length of the rod member 1120, as shown the first segment 1119 is coupled to first mounting eyelet 1150 by way of a threaded portion 1123. The first segment 1119 can be rotated around the threaded portion 1123 to form different lengths of the rod member 1120. Once a desired length is reached, the location of the first segment 1119 can be fixed by a locking nut 1227 disposed on the threaded portion 1123 between the first segment 1119 and the first mounting eyelet 1150. The first segment 1119 can be selectively unlocked with respect to the threaded portion 1123 and the second segment 1121 and subsequently adjusted as desired. Other mechanisms for locking a location of at least one of the two segments 1119, 1121 can also be used. As also shown in the illustrated embodiment, the anchor members 1170 disposed in the first and second mounting eyelets 1150, 1151 may extend at different angles due to the polyaxial seating of the anchor members within the eyelets 1150, 1151.

Figure 18A:
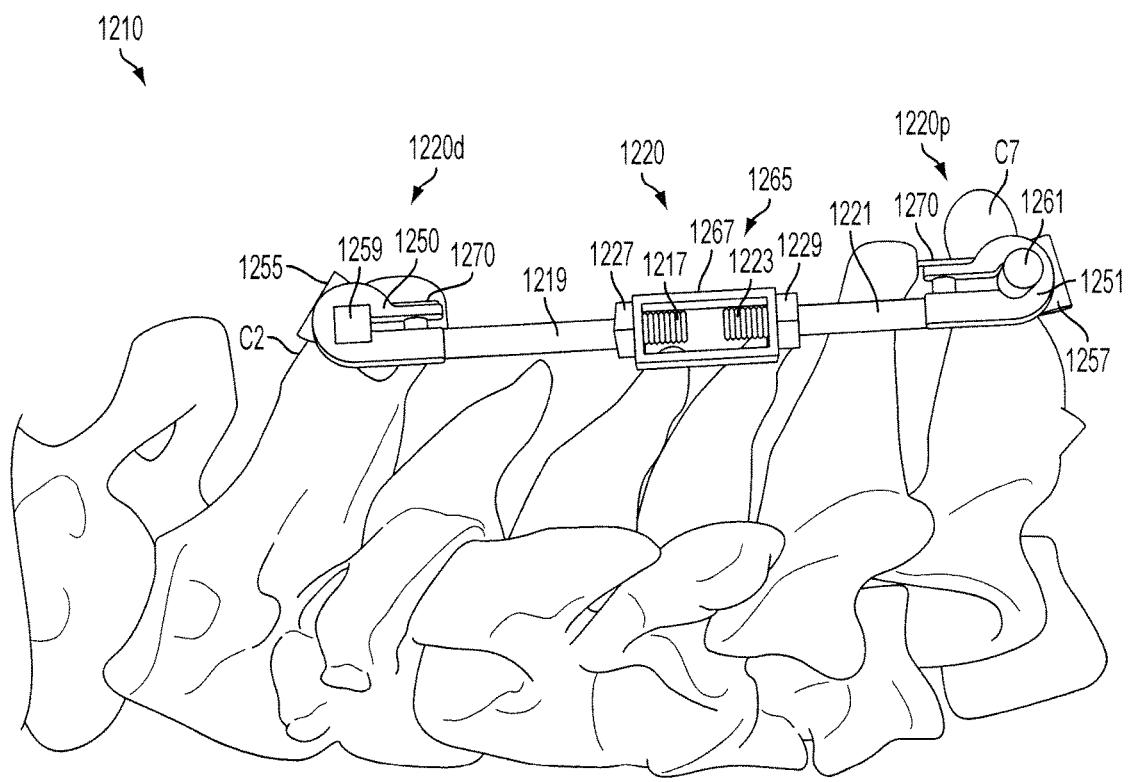
FIG. 18A is a perspective view of an exemplary embodiment of a spinal implant having a locking mechanism disposed between two segments of a rod member and being attached to a cervical region of a spine.
Figure 18B:
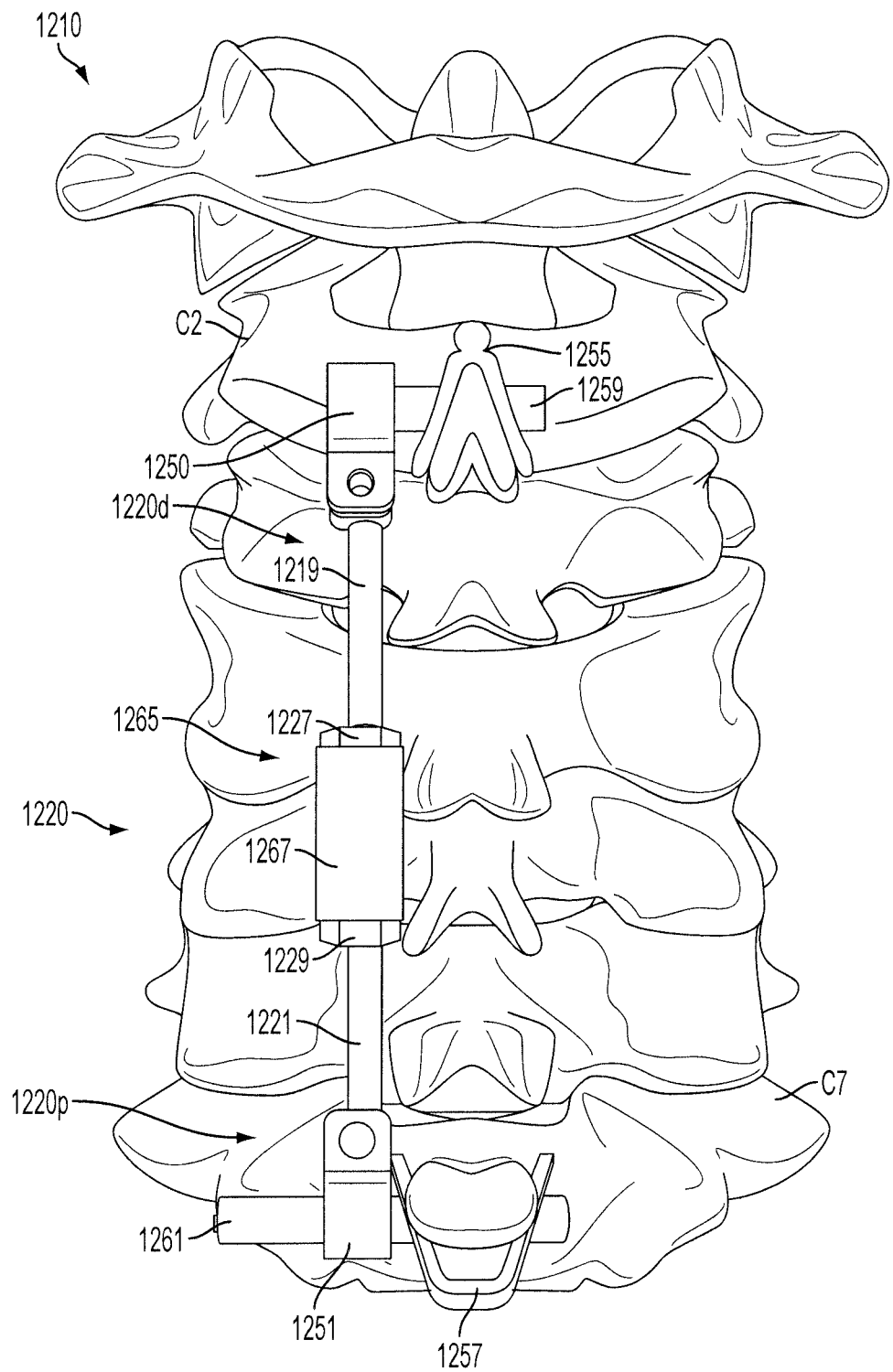
FIG. 18B is a perspective view of the spinal implant of FIG. 16A from the posterior side.
Figure 18C:
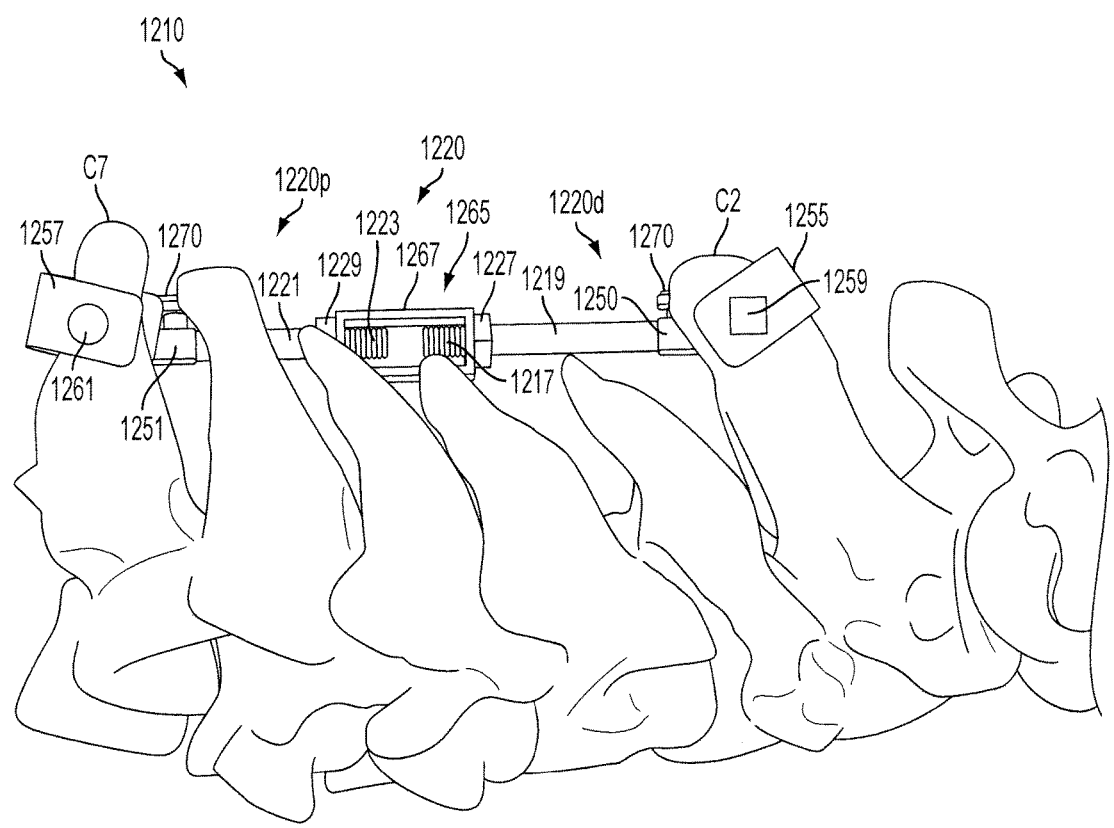
FIG. 18C is a perspective view of the spinal implant of FIG. 16A from a lateral side.

Another embodiment of a telescoping spinal fixation element implant 1210 that includes a rod member 1220 having an adjustable length is shown in FIGS. 18A-18C. A first mounting eyelet 1250 is secured to the spinous process of a first vertebra, C2, and a second mounting eyelet 1251 is secured to the spinous process of a second vertebra, C7. As shown in FIG. 18B, each of the two mounting eyelets 1250 and 1251 is secured to the respective C2 and C7 vertebrae by way of brackets 1255, 1257 and rods 1259, 1261. The brackets 1255, 1257 can be disposed around the spinous processes and the rods 1259, 1261 can be coupled to the brackets 1255, 1257 and eyelets 1250, 1251, passing through the spinous processes of the C2 and C7 vertebrae. One or more anchor members 1270 can be inserted proximate to the mounting eyelets 1250, 1251 to further secure the location of the eyelets 1250, 1251 with respect to the spine.

The rod member 1220 includes two separate segments 1219, 1221 disposed between the first and second eyelets 1250, 1251 and an adjustment mechanism 1265 is provided between the two segments 1219, 1221. As illustrated, the adjustment mechanism 1265 includes a locking member having a housing 1267. Threaded ends 1217, 1223 of each of the two segments 1219, 1221 are coupled to opposite ends of the housing 1267, and a portion of the threaded ends 1217, 1223 can be disposed within the hollow interior of the housing 1267. Locking nuts 1227, 1229 can be disposed around the segments 1219, 1221 on the outside of the housing 1267. As will be appreciated by a person skilled in the art, the locking nuts 1227, 1229 can be rotated to selectively lock and unlock the segments 1219, 1221 to form a rod of a desired length.

Figure 19:
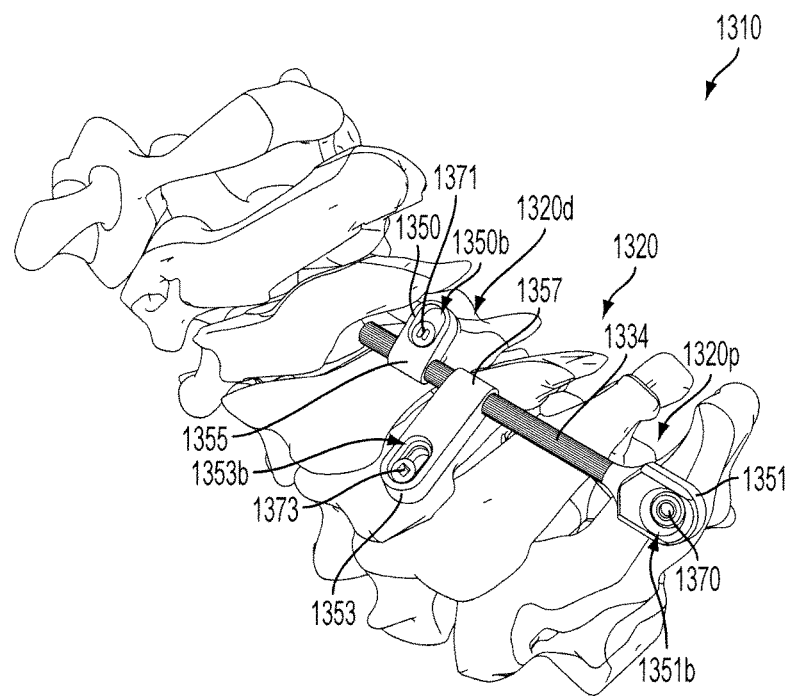
FIG. 19 is a perspective view of another exemplary embodiment of a spinal implant having three mounting eyelets and being attached to a cervical region of a spine.

FIG. 19 illustrates yet another embodiment of a spinal implant 1310 in which the spinal fixation element is a rod member 1320 that includes three mounting eyelets 1350, 1351, and 1353. As shown, eyelet 1351 is disposed at a proximal end 1320*p* of a rod member 1320 and is configured to be generally stationary. A bore 1351*b* of the eyelet 1351 is configured to receive an anchor member 1370 therein, and the size of the bore 1351*b* is generally complementary to a size of the anchor member 1370 to be disposed therein. As shown, the eyelet 1351 is integrated within the rod member 1320.

Mounting eyelet 1350 is shown disposed proximate to a distal end 1320*d* of the rod member 1320 and it is coupled to the rod member 1320 by way of a coupling portion 1355 disposed around at least a portion of the rod member 1320. The position of the coupling portion 1355 is adjustable as it can slide proximally and distally along the rod member to optimize the point of attachment to a vertebral body. The rod member 1320 can be substantially rigid, and it can include mating features, such as ridges 1334, that allow the coupling portion 1355 to more easily grip the rod member 1320. The diameter of a bore 1350*b* of the eyelet 1350 can be substantially larger than a diameter of an anchor member 1371 disposed therein. This configuration allows for fine adjustment of the relative position of the rod member 1320 and the anchor member 1371 when the anchor member 1371 is not fully seated within the bore 1350*b*. That is, the rod member 1320 can be slid in a direction toward and away from mounting eyelet 1350. When the anchor member 1371 is not fully secured in the eyelet, the anchor member 1371 can be rotated in a clockwise direction to engage the fixation element 1371 with the bore 1350*b*. This causes the coupling portion 1355 to tighten around the rod member 1320, thereby locking the first mounting eyelet 1350 and the rod member 1320 in place to set the new location of the rod member 1320.

Similarly, the diameter of a bore 1353*b* of the mounting eyelet 1353 is also larger than the diameter of an anchor member 1373 disposed therein and the third mounting eyelet 1353 is coupled to the rod member 1320 by way of a coupling portion 1357 disposed around at least a portion of the rod member 1320. As a result, adjustments to a location of the rod member 1320 and the coupling portion 1357 can be achieved in a similar manner as described with respect to the first mounting eyelet 1350.

Figure 20:
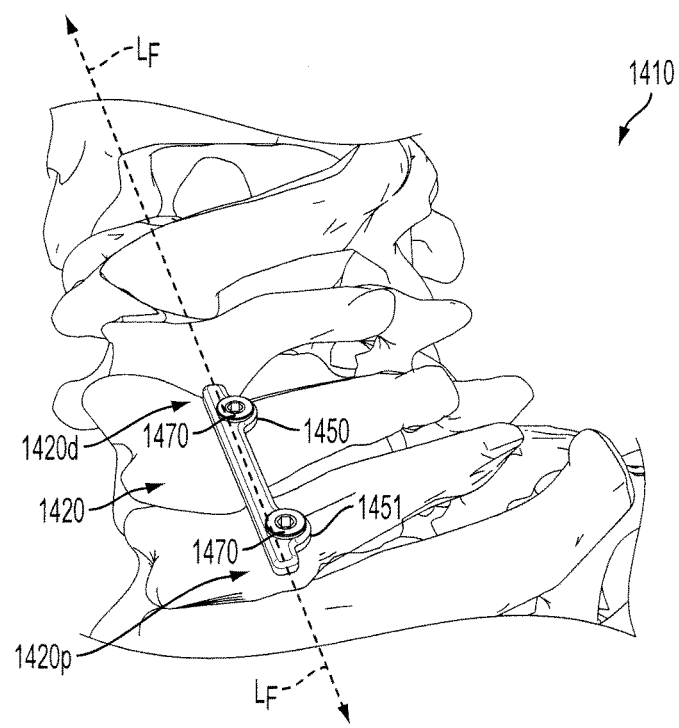
FIG. 20 is a perspective view of yet another exemplary embodiment of a spinal implant that is generally thin and flat and is attached to a cervical region of a spine.
Figure 21A:
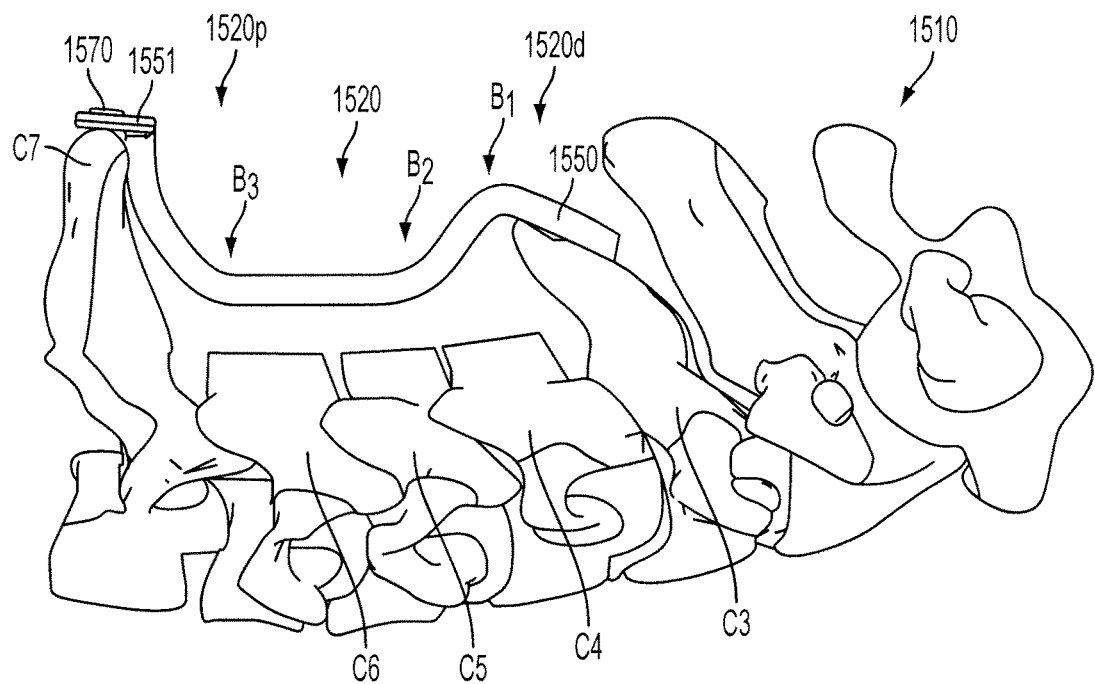
FIG. 21A is a perspective view of still another exemplary embodiment of a spinal implant having a plurality of bends in its shape and that is attached to a cervical region of a spine.
Figure 21B:
FIG. 21B is a perspective view of the spinal implant of FIG. 19A.

FIGS. 20, 21A, and 21B illustrate two further embodiments of implants 1410 and 1510 having differently shaped rod members 1420 and 1520. As shown in FIG. 20, the rod member 1420 is substantially thin and flat. In some embodiments the rod 1420 can be laminar in nature. The rod member 1420 illustrated in FIG. 20 includes two mounting eyelets 1450 and 1451, the first eyelet 1450 located in proximity to a distal end 1420*d* of the rod member 1420 and the second eyelet 1451 located in proximity to a proximal end 1420*p* of the rod member 1420. As shown, each of the two eyelets 1450, 1451 is offset with respect to a longitudinal axis $L_F$ of the rod member 1420, however, in other embodiments, one or more eyelets can be substantially in-line with the longitudinal axis $L_F$. Anchor members 1470 can be disposed in bores of the eyelets 1450, 1451.

FIGS. 21A and 21B illustrate a spinal implant 1510 having a rod member 1520 that includes a plurality of bends $B_1$, $B_2$, and $B_3$. As shown, the anatomy of the spine in which the rod member 1520 is disposed includes three vertebrae, C4, C5, and C6, in which the spinous process is cut away. The rod member 1520 bends closer to these portions of the vertebrae to provide additional stability. A distal end 1520d of the rod member 1520 includes a first mounting eyelet 1550 and is mounted to the spinous process of the C3 vertebra using an anchor member 1570. A proximal end 1520p of the rod member 1520 includes a second mounting eyelet 1551 and is mounted to the spinous process of the C7 vertebra using an anchor member 1570. As shown in FIG. 21B, the eyelet 1550 is offset with respect to a longitudinal axis $L_S$ of the rod member 1520 and the eyelet 1351 is substantially in-line with respect to the longitudinal axis $L_S$. As shown, a first, distal bend $B_1$ is provided proximate to the spinous process of the C3 vertebra, and then a second, intermediate bend $B_2$ is provided proximate to the C4 and C5 vertebrae. A third, proximal bend $B_3$ is provided proximate to the C6 and C7 vertebrae so the rod member 1520 can bend in a superior direction and terminate at the second eyelet 1351, proximate to the posterior portion of the C7 vertebra.

Any material can be used to form the spinal fixation elements disclosed in FIGS. 14A-21B, including biologically-compatible materials used to form spinal fixation elements and partially and fully bioresorbable materials. Examples of materials suitable for use include titanium, titanium alloys, polyether ether ketone (PEEK), and reinforced PEEK. In instances in which it is desirable for the rod member to have some flexibility, or even be fully bendable, materials that include a shape metal alloy, such as Nitinol®, can be desirable. Different portions of the length of spinal fixation elements can be made from different materials to achieve different desired results. Thus, a portion of the spinal fixation element can be made from a more flexible material while another portion of the spinal fixation element can be made from a more rigid material. Materials can be mixed and matched as desired.

In a method of use for implants illustrated and described with respect to FIGS. 14A-21B, an incision or delivery aperture can be formed proximate to a cervical region of the spine in a manner similar to the described incision formation with respect to the implants of FIGS. 2A-3, and the implant are is prepared as needed. For example, a lateral or posterior-lateral incision can be formed in an area near the cervical region of the spine and a rod member 920 can be inserted through to the cervical region of the spine directly or through an access port placed in the incision. An angle of insertion can be substantially perpendicular to the sagittal plane of a subject, or it can be at an angle posterior to perpendicular to the sagittal plane, as shown for example in FIG. 1. For reference purposes, unless specifically stated, the embodiment illustrated in FIG. 14B is discussed herein, although the methods can be used with respect to any of the spinal implants disclosed herein.

The rod member 920 can be inserted at a position that is lateral to or posterior-lateral to the cervical region of the spine. The rod member 920 can then be positioned proximate to the cervical region of the spine at a desired location. Eyelets 950, 951 of the rod member 920 can be aligned with the vertebrae in which they will be delivered. In the illustrated embodiment, the first mounting eyelet 950 is disposed proximate to the C3 vertebra and the second mounting eyelet 951 is disposed proximate to the C7 vertebra. Then each of the mounting eyelets 950, 951 can be attached to the respective vertebrae, C3 and C7, for example by using anchor members 970. This can be accomplished in any order, including simultaneously if the fixation element delivery device is designed in such a manner.

If desired, a second rod member 920 can also be introduced to the cervical region of the spine in the same manner. As shown in FIG. 14B, the second rod member 920 can be arranged to be substantially parallel to the first rod member 920.

In embodiments that are configured to permit segments of the rod member to slide with respect to each other, such as the embodiments illustrated in FIGS. 17A-18C, the method can include adjusting a length of the rod member between the first and second mounting eyelets. The length adjustment can occur at any time during the installation process, including before any of the eyelets are fixed to a vertebra, or after one or more of the eyelets are fixed to respective vertebrae. Even after the rod member is fully fixed at its proximal and distal ends, a length of the rod member can be adjusted to pull vertebrae apart or push them together as desired. Similarly, in embodiments that are configured to permit a location of mounting eyelets and rod members to be adjusted with respect to each other, the method can include adjusting locations of one or more mounting eyelets and one or more rod members with respect to each other to achieve a desired configuration at the surgical site.

Likewise, a shape of the rod members can be adjusted as part of the installation process. While the rod members can have a pre-determined shape, the rod members can also be either slightly flexible to allow for some minor shape changes on-site, or they can be fully bendable to allow for any number of shapes to be formed during a surgical procedure. This can allow for rod members to be shaped consistent with a profile of the spine.

Although the implants discussed herein are generally discussed with respect to being used in a cervical region of a spine, the implants can also be used in other regions of the spine, such as the thoracic and lumbar regions, as well as in other skeletal structures of a subject, such as skulls, femurs, tibias, and hips Likewise, although the implantation technique is generally described as being a lateral approach, the implants disclosed herein can be used in other approaches and in other locations in a subject.

One skilled in the art will appreciate further features and advantages of the invention based on the above-described embodiments. Accordingly, the invention is not to be limited by what has been particularly shown and described, except as indicated by the appended claims. A person skilled in the art will be able to apply features disclosed in one implant and generally apply those features to other implants as well because many of the features described herein are capable of being mixed and matched across various embodiments. All publications and references cited herein are expressly incorporated herein by reference in their entirety.

What is claimed is:

1. An implantable spinal fixation device, comprising:
a continuous, unitary elongate rod member having a main body extending from a proximal terminal end to a distal terminal end to constitute a length of the rod member, the main body having a substantially circular or ovoid cross sectional shape;
a first mounting eyelet formed on the elongate rod member in proximity to the distal end of the rod member and having an opening formed therein, the opening having a first central axis extending therethrough, the first central axis intersecting the length and a longitudinal axis that extends between the proximal and distal terminal ends of the rod member; and
a second mounting eyelet formed on the elongate rod member remote from the first mounting eyelet and distal of the proximal terminal end, the second mounting eyelet having an opening formed therein that has a second central axis extending therethrough, the second central axis being offset from each of the length, the proximal terminal end, and the longitudinal axis that extends between the proximal and distal terminal ends of the rod member, the first and second mounting eyelets being configured to be fixedly located with respect to each other at all times, wherein top surfaces of the first and second mounting eyelets are not collinear,
wherein the main body of the rod member is curved in at least one plane along its length such that one side of the main body of the rod member has a concave portion and an opposed side of the main body of the rod member has a concurrent convex portion when viewed from a plane that is perpendicular to a central axis that extends through the opening of the second mounting eyelet without contacting a body of the second mounting eyelet and which is parallel to a plane extending through a substantial length of the main body of the rod member,
wherein the second mounting eyelet comprises an extension formed laterally offset from the main body of the elongate rod member; and
wherein the direction of curvature of the concave and convex portions is towards the second mounting eyelet.

2. The device of claim 1, further comprising a third mounting eyelet coupled to the elongate rod member, the third mounting eyelet being disposed between the first mounting eyelet and the second mounting eyelet.

3. The device of claim 2, wherein the third mounting eyelet is slidable with respect to the elongate rod member.

4. The device of claim 3, further comprising a securing member configured to set a location of the third mounting eyelet with respect to the rod member.

5. The device of claim 2, further comprising an anchor member configured to be located offset from the elongate rod member, the anchor member being coupled to the third mounting eyelet by way of a connector.

6. The device of claim 5, wherein the connector is coupled to the anchor member and to the third mounting eyelet, the third mounting eyelet being slidable such that a location of the connector with respect to the rod member is adjustable by sliding the third mounting eyelet along the rod member.

7. The device of claim 2, wherein the third mounting eyelet is disposed along the rod member such that the third mounting eyelet does not intersect either of the first mounting eyelet or the second mounting eyelet.

8. The device of claim 2, further comprising:
an anchor member configured to be located offset from the elongate rod member, the anchor member being coupled to the third mounting eyelet by way of a connector,
wherein the third mounting eyelet is configured to be selectively secured to the rod member such that a location of the connector with respect to the rod member is adjustable.

9. The device of claim 1, wherein the first and second eyelets are configured to each receive screws to anchor the implantable spinal fixation device against the spine.

10. The device of claim 9, further comprising:
a first screw; and
a second screw,
wherein the first eyelet receives the first screw to anchor the implantable spinal fixation device against the spine, and
wherein the second eyelet receives the second screw to anchor the implantable spinal fixation device against the spine.

11. The device of claim 1, wherein the second mounting eyelet is in proximity to the proximal end of the main body of the rod member.

12. The device of claim 1, wherein the first mounting eyelet is at the distal end of the elongate rod member.

13. The device of claim 1, wherein the first and second mounting eyelets are of a unitary construction with the rod member.

14. The device of claim 1, further comprising a notch formed in a surface of the rod member at a location between the second mounting eyelet and the proximal terminal end of the rod member.

15. An implantable spinal fixation device, comprising:
a continuous, unitary elongate rod member extending from a proximal terminal end to a distal terminal end to constitute a length of the rod member;
a first mounting eyelet formed on the elongate rod member in proximity to the distal terminal end of the rod member and having a central lumen extending therethrough, the central lumen having a first central axis extending therethrough, the first central axis intersecting the length and a longitudinal axis that extends between the proximal and distal terminal ends of the rod member; and
a second mounting eyelet formed on the elongate rod member in proximity to the proximal. terminal end of the rod member and having an central lumen extending therethrough, the central lumen having a second central axis extending therethrough, the second central axis being offset from the length and the central longitudinal axis that extends along the rod member between the proximal and distal terminal ends of the rod member, the first and second mounting eyelets being configured to be fixedly located with respect to each other at all times, wherein top surfaces of the first and second mounting eyelets are not collinear,
wherein, when viewed from a plane that is perpendicular to a central axis that extends through the opening of the second mounting eyelet without contacting a body of the second mounting eyelet, and which is parallel to a plane extending through a substantial length of the rod member, the rod member is curved along its length such that one side of the rod member has a concave portion extending along a majority of the length of the rod and an opposed side of the rod member has a concurrent convex portion extending along a majority of the length of the rod, with the direction of curvature of the concave and convex portions being towards the second mounting eyelet.

16. The device of claim 15, further comprising a third mounting eyelet selectively adjustably coupled to the elongate rod member, the third mounting eyelet being disposed between the first mounting eyelet and the second mounting eyelet.

17. The device of claim 16, further comprising an anchor member configured to be located offset from the elongate rod member, the anchor member being selectively adjustably coupled to the third mounting eyelet by way of a connector.

18. The device of claim 16, wherein the third mounting eyelet is disposed along the rod member such that the third mounting eyelet does not intersect either of the first mounting eyelet or the second mounting eyelet.

19. The device of claim 18, further comprising a securing member configured to set a location of the third mounting eyelet with respect to the rod member.

20. The device of claim 15, wherein the second mounting eyelet is in proximity to the proximal end of the rod member.

21. The device of claim 20, wherein the second mounting eyelet is distal of the proximal terminal end of the rod member.

* * * * *